US007732187B2

(12) United States Patent
Cochran et al.

(10) Patent No.: US 7,732,187 B2
(45) Date of Patent: Jun. 8, 2010

(54) RECOMBINANT ATTENUATED CLOSTRIDIUM ORGANISMS AND VACCINE

(75) Inventors: Mark D. Cochran, Carlsbad, CA (US); Gary R. Petersen, Omaha, NE (US); Stephen V. Lair, Temecula, CA (US); Richard M. Synenki, San Diego, CA (US)

(73) Assignee: Intervet Inc., Roseland, NJ (US)

( * ) Notice: Subject to any disclaimer, the term of this patent is extended or adjusted under 35 U.S.C. 154(b) by 286 days.

(21) Appl. No.: 11/734,454

(22) Filed: Apr. 12, 2007

(65) Prior Publication Data

US 2007/0286874 A1 Dec. 13, 2007

Related U.S. Application Data

(60) Provisional application No. 60/792,553, filed on Apr. 17, 2006.

(51) Int. Cl.
C12N 1/20 (2006.01)
(52) U.S. Cl. .................. 435/252.7; 435/243; 435/252.1; 424/247.1; 424/200.1; 424/235.1
(58) Field of Classification Search ........................ None
See application file for complete search history.

(56) References Cited

U.S. PATENT DOCUMENTS

| 4,292,307 | A | 9/1981 | Zemlyakova |
| 5,817,317 | A | 10/1998 | Titball et al. |
| 5,851,827 | A | 12/1998 | Titball et al. |
| 6,403,094 | B1 | 6/2002 | Titball et al. |
| 6,610,300 | B1 | 8/2003 | Segers et al. |
| 2006/0233825 | A1 | 10/2006 | Jayappa et al. |

FOREIGN PATENT DOCUMENTS

| GB | 1 483 042 | 8/1977 |
| WO | WO 02/07741 A1 | 1/2002 |

OTHER PUBLICATIONS

Alape-Girón et al., "Identification of residues critical for toxicity in Clostridium perfringens phospholipase C, the key toxin in gas gangrene", Eur. J. Biochem. 267:5191-5197 (2000).
Allen and Blaschek, "Electroporation-induced transformation of intact cells of Clostridium perfringens", Applied and Environmental Microbiology, 54(9):2322-2324 (1988).
Al-Sheikhly and Truscott, "The Interaction of Clostridium perfringens and its Toxins in The production of Necrotic Enteritis of Chickens", Avian Dis. 21(2):256-263 (1977).
Bannam and Rood, "Clostridium perfringens-Escherichia coli Shuttle Vectors That Carry Single Antibiotic Resistance Determinants", Plasmid 229:233-235 (1993).
Bennett et at, "Recombinant Vaccinia Viruses Protect Against Clostridium perfringens αToxin", Viral Immunol. 12(2):97-105 (1999).
Ficken and Wages, "Clostridial Diseases. Necrotic Enteritis", Diseases of Poultry, 10th Ed., pp. 261-264 (1997).

Justin et al., "The First Strain of Clostridium pefringens Isolated from an Avian Source Has an Alpha-Toxin with Divergent Structural and Kinetic Properties", Biochemistry 41(20):6253-6262 (2002).
Kim et al., "Construction of an Escherichia coli-Clostridium perfringens shuttle vector and plasmid transformation of Clostridium perfringens", Appl Environ Microbiol 55(2):360-365.
Logan et al., "Epitope mapping of the alpha-toxin of Clostridium perfringens", Infection and Immunity, 59(12):4338-4342 (1991).
Lovland and Kaldhusdal, "Severely impaired production performance in broiler flocks with high incidence of Clostridium perfringens-associated hepatitis", Avian Pathology 30:73-81 (2001).
Lovland et at, "Maternal vaccination against subclinical necrotic enteritis in broilers", Avian Pathology 33(1):83-92 (2004).
Lyras et al., "Short Communication. Conjugative Transfer of RP4-oriT Shuttle Vectors from Escherichia coli to Clostridium perfringens", Plasmid 39(2):160-164 (1998).
Matsushita et al., "A Clostridium perfringens Vector for the Selection of Promoters", Plasmid 31(3):317-319 (1994).
Nagahama at al., "Site-directed mutagenesis of histidine residues in Clostridium perfringens alpha-toxin", J. Bacteriology 177(5):1179-1185 (1995).
Nagahama et al., "Site-specific mutagenesis of Clostridium perfringens alpha-toxin: replacement of Asp-56, Asp-130, or Glu-152 causes loss of enzymatic and hemolytic activities", Infect. and Immun. 65(8):3489-3492 (1997).
Pearson et al., "Hemorrhagic enteritis caused by Clostridium perfringens type C in a foal", J. Am. Vet. Med. 188(11):1309-1310 (1986).
Roberts et al., "Development of a new shuttle plasmid system for Escherichia coil and Clostridium perfringens", Appl Env Mircobiol 54(1):268-270 (1988).
Schoepe at al., "Naturally Occurring Clostridium perfringens Nontoxic Alpha-Toxin Variant as a Potential Vaccine Candidate against Alpha-Toxin-Associated Diseases", Infect. and Immun. 69(11):7194-7196 (2001).
Schoepe et al., "Immunization with an alphatoxin variant 121A/91-R212H protects mice against Clostridium perfringens alphatoxin", Anaerobe 12(1):44-48 (2006).
Sloan at aL, "Construction of a sequenced Clostridium perfringens-Escherichia coil shuttle plasmid", Plasmid 27(3):207-219 (1992).
Stevens et al., "Immunization with the C-domain of alpha-toxin prevents lethal infection, localizes tissue injury, and promotes host response to challenge with Clostridium perfringens", Journal of Infectious Diseases, 190(4):767-773 (2004).
Tsutsui et al., "Phylogenetic Analysis of Phospholipase C Genes from Clostridium perfringens Types A to E and Clostridium novyl", Journal of Bacteriology, 177(24):7164-7170 (1995).
Williamson and Titball, "A genetically engineered vaccine against the alpha-toxin of Clostridium perfringens protects mice against experimental gas gangrene", Vaccine 11(12):1253-1258 (1993).
International Search Report dated Jan. 22, 2008, for corresponding International Application No. PCT/US2007/009135; Applicant: Schering-Plough Ltd.

Primary Examiner—Jennifer E Graser

(57) ABSTRACT

The present invention discloses attenuated Clostridium perfringens organisms that express a substantially nontoxic alpha-toxin. The expressed alpha-toxin is a deletion mutein that relative to the alpha-toxin of the mature alpha-toxin of Clostridium perfringens strain 13, is missing at least nine consecutive amino acid residues including $His_{68}$. The present invention also discloses attenuated organisms that encode the muteins, as well as the use of such attenuated organisms as vaccines.

29 Claims, 3 Drawing Sheets

FIG. 2A

SEQ ID NO: 4  -AAC GCC TAT GAT CTA TAT CAA GAT CAT TTC TG<u>G GAT CCT</u>-
SEQ ID NO: 5  -Asn Ala Tyr Asp Leu Tyr Gln Asp His Phe Trp Asp Pro-

FIG. 2B

SEQ ID NO: 6  -AAT GCa tt<u>g gat cc</u>
SEQ ID NO: 7  -Asn Ala Leu Asp

FIG. 2C

SEQ ID NO: 8          -AAT GCA TT<u>G GAT CCT</u>-
SEQ ID NO: 9          -Asn Ala Leu Asp Pro-

FIG. 3A

SEQ ID NO: 4   -AAC GCC TAT GAT CTA TAT CAA GAT CAT TTC TGG GAT CCT-
SEQ ID NO: 5   -Asn Ala Tyr Asp Leu Tyr Gln Asp His Phe Trp Asp Pro-

FIG. 3B

SEQ ID NO: 10   -AAT GCG gat cca gt
SEQ ID NO: 11   -Asn Ala Asp Pro

FIG. 3C

SEQ ID NO: 12            -AAT GCG GAT CCT-
SEQ ID NO: 13            -Asn Ala Asp Pro-

SEQUENCE LISTING

```
<160> NUMBER OF SEQ ID NOS: 23

<210> SEQ ID NO 1
<211> LENGTH: 398
<212> TYPE: PRT
<213> ORGANISM: Clostridium perfringens strain 13

<400> SEQUENCE: 1

Met Lys Arg Lys Ile Cys Lys Ala Leu Ile Cys Ala Thr Leu Ala Thr
1               5                   10                  15

Ser Leu Trp Ala Gly Ala Ser Thr Lys Val Tyr Ala Trp Asp Gly Lys
            20                  25                  30

Ile Asp Gly Thr Gly Thr His Ala Met Ile Val Thr Gln Gly Val Ser
        35                  40                  45

Ile Leu Glu Asn Asp Leu Ser Lys Asn Glu Pro Glu Ser Val Arg Lys
    50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
    130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Ala Gly Cys Lys Thr Asn Glu Asp Phe Tyr Ala Asp Ile Leu
        195                 200                 205

Lys Asn Lys Asp Phe Asn Ala Trp Ser Lys Glu Tyr Ala Arg Gly Phe
    210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Lys Asn Val Lys Glu Leu Val Ala
        275                 280                 285

Tyr Ile Ser Thr Ser Gly Glu Lys Asp Ala Gly Thr Asp Asp Tyr Met
    290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
                325                 330                 335

Phe Lys Leu Lys Asp Glu Asn Leu Lys Ile Asp Asp Ile Gln Asn Met
            340                 345                 350

Trp Ile Arg Lys Arg Lys Tyr Thr Ala Phe Pro Asp Ala Tyr Lys Pro
```

|     |     |     |     |     | 355 |     |     |     | 360 |     |     |     |     | 365 |     |
| --- | --- | --- | --- | --- | --- | --- | --- | --- | --- | --- | --- | --- | --- | --- | --- |

Glu Asn Ile Lys Ile Ile Ala Asn Gly Lys Val Val Asp Lys Asp
    370                        375                       380

Ile Asn Glu Trp Ile Ser Gly Asn Ser Thr Tyr Asn Ile Lys
385                     390                     395

<210> SEQ ID NO 2
<211> LENGTH: 1197
<212> TYPE: DNA
<213> ORGANISM: Clostridium perfringens strain 13

<400> SEQUENCE: 2

```
atgaaagaa agatttgtaa ggcgcttatt tgtgctacgc tagcaactag cctatgggct     60
ggggcatcaa ctaaagtcta cgcttgggat ggaaagattg atggaacagg aactcatgct    120
atgattgtaa ctcaagggt ttcaatctta gaaaatgatc tgtccaaaaa tgaaccagaa    180
agtgtaagaa aaaacttaga gattttaaaa gagaacatgc atgagcttca attaggttct    240
acttatccag attatgataa gaatgcatat gatctatatc aagatcattt ctgggatcct    300
gatacagata taattttctc aaaggataat agttggtatt tagcttattc tatacctgac    360
acaggggaat cacaaataag aaaattttca gcattagcta gatatgaatg caaagagga    420
aactataaac aagctacatt ctatcttgga gaggctatgc actattttgg agatatagat    480
actccatatc atcctgctaa tgttactgcc gttgatagcg caggacatgt taagtttgaa    540
acttttgcag aggaaagaaa agaacagtat aaaataaaca cagcaggttg caaaactaat    600
gaggattttt atgctgatat cttaaaaaac aaggatttta tgcatggtc aaaagaatat    660
gcaagaggtt ttgctaaaac aggaaaatca atatactata gtcatgctag catgagtcat    720
agttgggatg attgggatta tgcagcaaag gtaactttag ctaactctca aaaaggaaca    780
gcaggatata tttatagatt cttacacgat gtatcagagg gtaatgatcc atcagttgga    840
aagaatgtaa agaactagt agcttacata tcaactagtg gtgaaaaaga tgctggaaca    900
gatgactaca tgtattttgg aatcaaaaca aaggatggaa aaactcaaga atgggaaatg    960
gacaacccag gaaatgattt tatgactgga agtaaagaca cttatacttt caaattaaaa   1020
gatgaaaatc taaaaattga tgatatacaa aatatgtgga ttagaaaaag aaatatacaa   1080
gcattcccag atgcttataa gccagaaaac ataaagataa tagcaaatgg aaaagttgta   1140
gtagacaaag atataaatga gtggatttca ggaaattcaa cttataatat aaaataa    1197
```

<210> SEQ ID NO 3
<211> LENGTH: 370
<212> TYPE: PRT
<213> ORGANISM: Clostridium perfringens strain 13

<400> SEQUENCE: 3

Trp Asp Gly Lys Ile Asp Gly Thr Gly Thr His Ala Met Ile Val Thr
1                  5                    10                  15

Gln Gly Val Ser Ile Leu Glu Asn Asp Leu Ser Lys Asn Glu Pro Glu
                20                    25                    30

Ser Val Arg Lys Asn Leu Glu Ile Leu Lys Glu Asn Met His Glu Leu
        35                    40                  45

Gln Leu Gly Ser Thr Tyr Pro Asp Tyr Asp Lys Asn Ala Tyr Asp Leu
                50                    55                    60

Tyr Gln Asp His Phe Trp Asp Pro Asp Thr Asp Asn Asn Phe Ser Lys
65                  70                    75                    80

```
Asp Asn Ser Trp Tyr Leu Ala Tyr Ser Ile Pro Asp Thr Gly Glu Ser
                85                  90                  95

Gln Ile Arg Lys Phe Ser Ala Leu Ala Arg Tyr Glu Trp Gln Arg Gly
            100                 105                 110

Asn Tyr Lys Gln Ala Thr Phe Tyr Leu Gly Glu Ala Met His Tyr Phe
        115                 120                 125

Gly Asp Ile Asp Thr Pro Tyr His Pro Ala Asn Val Thr Ala Val Asp
    130                 135                 140

Ser Ala Gly His Val Lys Phe Glu Thr Phe Ala Glu Arg Lys Glu
145                 150                 155                 160

Gln Tyr Lys Ile Asn Thr Ala Gly Cys Lys Thr Asn Glu Asp Phe Tyr
                165                 170                 175

Ala Asp Ile Leu Lys Asn Lys Asp Phe Asn Ala Trp Ser Lys Glu Tyr
            180                 185                 190

Ala Arg Gly Phe Ala Lys Thr Gly Lys Ser Ile Tyr Tyr Ser His Ala
        195                 200                 205

Ser Met Ser His Ser Trp Asp Asp Trp Asp Tyr Ala Ala Lys Val Thr
    210                 215                 220

Leu Ala Asn Ser Gln Lys Gly Thr Ala Gly Tyr Ile Tyr Arg Phe Leu
225                 230                 235                 240

His Asp Val Ser Glu Gly Asn Asp Pro Ser Val Gly Lys Asn Val Lys
                245                 250                 255

Glu Leu Val Ala Tyr Ile Ser Thr Ser Gly Glu Lys Asp Ala Gly Thr
            260                 265                 270

Asp Asp Tyr Met Tyr Phe Gly Ile Lys Thr Lys Asp Gly Lys Thr Gln
        275                 280                 285

Glu Trp Glu Met Asp Asn Pro Gly Asn Asp Phe Met Thr Gly Ser Lys
    290                 295                 300

Asp Thr Tyr Thr Phe Lys Leu Lys Asp Glu Asn Leu Lys Ile Asp Asp
305                 310                 315                 320

Ile Gln Asn Met Trp Ile Arg Lys Arg Lys Tyr Thr Ala Phe Pro Asp
                325                 330                 335

Ala Tyr Lys Pro Glu Asn Ile Lys Ile Ile Ala Asn Gly Lys Val Val
            340                 345                 350

Val Asp Lys Asp Ile Asn Glu Trp Ile Ser Gly Asn Ser Thr Tyr Asn
        355                 360                 365

Ile Lys
    370

<210> SEQ ID NO 4
<211> LENGTH: 39
<212> TYPE: DNA
<213> ORGANISM: Clostridium perfringens

<400> SEQUENCE: 4
aacgcctatg atctatatca agatcatttc tgggatcct                          39

<210> SEQ ID NO 5
<211> LENGTH: 13
<212> TYPE: PRT
<213> ORGANISM: Clostridium perfringens

<400> SEQUENCE: 5

Asn Ala Tyr Asp Leu Tyr Gln Asp His Phe Trp Asp Pro
1               5                   10
```

-continued

```
<210> SEQ ID NO 6
<211> LENGTH: 14
<212> TYPE: DNA
<213> ORGANISM: Artificial
<220> FEATURE:
<223> OTHER INFORMATION: Chemically synthesized

<400> SEQUENCE: 6
aatgcattgg atcc                                                          14

<210> SEQ ID NO 7
<211> LENGTH: 4
<212> TYPE: PRT
<213> ORGANISM: Artificial
<220> FEATURE:
<223> OTHER INFORMATION: Amino acid sequence contained/inserted into
      protein after a deletion. Can be chemically synthesized

<400> SEQUENCE: 7

Asn Ala Leu Asp
1

<210> SEQ ID NO 8
<211> LENGTH: 15
<212> TYPE: DNA
<213> ORGANISM: Artificial
<220> FEATURE:
<223> OTHER INFORMATION: Chemically synthesized

<400> SEQUENCE: 8
aatgcattgg atcct                                                         15

<210> SEQ ID NO 9
<211> LENGTH: 5
<212> TYPE: PRT
<213> ORGANISM: Artificial
<220> FEATURE:
<223> OTHER INFORMATION: Amino acid sequence contained by/inserted into
      protein after a deletion. Can be chemically synthesized

<400> SEQUENCE: 9

Asn Ala Leu Asp Pro
1               5

<210> SEQ ID NO 10
<211> LENGTH: 14
<212> TYPE: DNA
<213> ORGANISM: Artificial
<220> FEATURE:
<223> OTHER INFORMATION: Chemically synthesized

<400> SEQUENCE: 10
aatgcggatc cagt                                                          14

<210> SEQ ID NO 11
<211> LENGTH: 4
<212> TYPE: PRT
<213> ORGANISM: Artificial
<220> FEATURE:
<223> OTHER INFORMATION: Amino acid sequence contained/inserted into
      protein after a deletion. Can be chemically synthesized

<400> SEQUENCE: 11

Asn Ala Asp Pro
1

<210> SEQ ID NO 12
```

<211> LENGTH: 12
<212> TYPE: DNA
<213> ORGANISM: Artificial
<220> FEATURE:
<223> OTHER INFORMATION: Chemically synthesized

<400> SEQUENCE: 12
aatgcggatc ct                                                          12

<210> SEQ ID NO 13
<211> LENGTH: 4
<212> TYPE: PRT
<213> ORGANISM: Artificial
<220> FEATURE:
<223> OTHER INFORMATION: Amino acid sequence contained by/inserted into
      protein after a deletion. Can be chemically synthesized

<400> SEQUENCE: 13

Asn Ala Asp Pro
1

<210> SEQ ID NO 14
<211> LENGTH: 26
<212> TYPE: DNA
<213> ORGANISM: Artificial
<220> FEATURE:
<223> OTHER INFORMATION: Chemically synthesized

<400> SEQUENCE: 14
agctgcataa gcaaaagttc caactc                                           26

<210> SEQ ID NO 15
<211> LENGTH: 33
<212> TYPE: DNA
<213> ORGANISM: Artificial
<220> FEATURE:
<223> OTHER INFORMATION: Chemically synthesized

<400> SEQUENCE: 15
gcagaaactc ttcttagacc tattctttta ggc                                   33

<210> SEQ ID NO 16
<211> LENGTH: 32
<212> TYPE: DNA
<213> ORGANISM: Artificial
<220> FEATURE:
<223> OTHER INFORMATION: Chemically synthesized

<400> SEQUENCE: 16
ggatccagct gcataagcaa aagttccaac tc                                    32

<210> SEQ ID NO 17
<211> LENGTH: 41
<212> TYPE: DNA
<213> ORGANISM: Artificial
<220> FEATURE:
<223> OTHER INFORMATION: Chemically synthesized

<400> SEQUENCE: 17
ggatccaatg cattcttatc ataatctgga taagtagaac c                          41

<210> SEQ ID NO 18
<211> LENGTH: 37
<212> TYPE: DNA
<213> ORGANISM: Artificial
<220> FEATURE:
<223> OTHER INFORMATION: Chemically synthesized

<400> SEQUENCE: 18
ctgggatcct gatacagata ataatttctc aaaggat                                37

<210> SEQ ID NO 19
<211> LENGTH: 40
<212> TYPE: DNA
<213> ORGANISM: Artificial
<220> FEATURE:
<223> OTHER INFORMATION: Chemically synthesized

<400> SEQUENCE: 19
actctgcagt tgtcatatca attaaattaa ctataatccc                             40

<210> SEQ ID NO 20
<211> LENGTH: 37
<212> TYPE: DNA
<213> ORGANISM: Artificial
<220> FEATURE:
<223> OTHER INFORMATION: Chemically synthesized

<400> SEQUENCE: 20
actgagctcc tagacacttt gcttcaatat ttgggaa                                37

<210> SEQ ID NO 21
<211> LENGTH: 41
<212> TYPE: DNA
<213> ORGANISM: Artificial
<220> FEATURE:
<223> OTHER INFORMATION: Chemically synthesized

<400> SEQUENCE: 21
actggatccg cattcttatc ataatctgga taagtagaac c                           41

<210> SEQ ID NO 22
<211> LENGTH: 1197
<212> TYPE: DNA
<213> ORGANISM: Clostridium perfringens strain CP6

<400> SEQUENCE: 22
atgaaaagaa agatttgtaa ggcgcttatt tgtgctgcgc tagcaactag cctatgggct        60
ggggcatcaa ctaaagtcta cgcttgggat ggaaaaattg atggaacagg aactcatgct       120
atgattgtaa ctcaagggt tcaatctta gaaaatgatc tgtctaaaaa tgaaccagaa         180
agtgtaagaa aaaacttaga gattttaaaa gagaacatgc atgagcttca attaggttct       240
acttatccag attatgataa aacgccta tgatctatatc aagatcattt ctgggatcct        300
gatacagata ataatttctc aaaggataat agttggtatt agcttattc tatacctgac        360 acaggggaat cacaaataag aaaatttca gcattagcta gatatgaatg caaagagga        420 aactataaac aagctacatt ctatcttgga gaggctatgc actattttgg agatatagat       480
actccatatc atcctgctaa tgttactgcc gttgatagcg caggacatgt taagtttgag       540
acttttgcag aggaaagaaa agaacagtat aaaataaaca cagcaggttg caaaactaat       600 gaggatttt atgctgatat cttaaaaaac aaagatttta atgcatggtc aaaagaatat       660
gcaagaggtt ttgctaaaac aggaaaatca atatactata gtcatgctag catgagtcat       720
agttgggatg attgggatta tgcagcaaag gtaactttag ctaactctca aaaggaaca       780 gcaggatata tttatagatt cttacacgat gtatcagagg gtaatgatcc atcagttgga       840
aagaatgtaa aagaactagt agcttacata tcaactagtg gtgaaaaaga tgctggaaca       900

-continued

```
gatgactaca tgtattttgg aatcaaaaca aaggatggaa aaactcaaga atgggaaatg    960
gacaacccag gaaatgattt tatgactgga agtaaagaca cttatacttt caaattaaaa   1020
gatgaaaatc taaaaattga tgatatacaa aatatgtgga ttagaaaaag aaaatataca   1080
gcattcccag atgcttataa gccagaaaac ataaagataa tagcaaatgg aaaagttgta   1140
gtagacaaag atataaatga gtggatttca ggaaattcaa cttataatat aaaataa     1197
```

<210> SEQ ID NO 23
<211> LENGTH: 398
<212> TYPE: PRT
<213> ORGANISM: Clostridium perfringens strain CP6

<400> SEQUENCE: 23

```
Met Lys Arg Lys Ile Cys Lys Ala Leu Ile Cys Ala Ala Leu Ala Thr
1               5                   10                  15

Ser Leu Trp Ala Gly Ala Ser Thr Lys Val Tyr Ala Trp Asp Gly Lys
                20                  25                  30

Ile Asp Gly Thr Gly Thr His Ala Met Ile Val Thr Gln Gly Val Ser
            35                  40                  45

Ile Leu Glu Asn Asp Leu Ser Lys Asn Glu Pro Glu Ser Val Arg Lys
        50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
                100                 105                 110

Tyr Leu Ala Tyr Ser Ile Pro Asp Thr Gly Glu Ser Gln Ile Arg Lys
            115                 120                 125

Phe Ser Ala Leu Ala Arg Tyr Glu Trp Gln Arg Gly Asn Tyr Lys Gln
        130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Ala Gly Cys Lys Thr Asn Glu Asp Phe Tyr Ala Asp Ile Leu
        195                 200                 205

Lys Asn Lys Asp Phe Asn Ala Trp Ser Lys Glu Tyr Ala Arg Gly Phe
    210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Lys Asn Val Lys Glu Leu Val Ala
        275                 280                 285

Tyr Ile Ser Thr Ser Gly Glu Lys Asp Ala Gly Thr Asp Asp Tyr Met
    290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
```

-continued

```
              325                 330                 335
Phe Lys Leu Lys Asp Glu Asn Leu Lys Ile Asp Asp Ile Gln Asn Met
            340                 345                 350

Trp Ile Arg Lys Arg Lys Tyr Thr Ala Phe Pro Asp Ala Tyr Lys Pro
            355                 360                 365

Glu Asn Ile Lys Ile Ile Ala Asn Gly Lys Val Val Val Asp Lys Asp
        370                 375                 380

Ile Asn Glu Trp Ile Ser Gly Asn Ser Thr Tyr Asn Ile Lys
385                 390                 395
```

RECOMBINANT ATTENUATED *CLOSTRIDIUM* ORGANISMS AND VACCINE

CROSS-REFERENCE TO RELATED APPLICATIONS

This application is a non-provisional application that claims priority under 35 U.S.C. § 119(e) of provisional applications U.S. Ser. No. 60/792,553 filed Apr. 17, 2006, the contents of which are hereby incorporated by reference in its entirety.

FIELD OF THE INVENTION

This invention is related to attenuated *Clostridium* organisms, methods of making and using the same, and mutein alpha-toxins and nucleic acids encoding the same.

BACKGROUND OF THE INVENTION

Anaerobic bacterial pathogens are a serious economic burden on the agricultural industry. Bacteria of the *Clostridium* family represent a particular burden, because these bacteria cause serious diseases in poultry and other economically valuable domestic animals. Previous efforts to control these organisms have relied upon sanitary measures and the administration of antibiotics in the animal feed.

In particular, *Clostridium perfringens* ("*C. perfringens*") is an anaerobic bacterium that is found in the soil, decaying organic matter, and as part of the gut flora of humans and animals. Different strains of *C. perfringens* are designated as biotypes A through E, depending on the spectrum of toxins produced [Justin et al., *Biochemistry* 41, 6253-6262 (2002); McDonel (1986) PHARMACOLOGY OF BACTERIAL TOXINS; F Dorner and J Drews (Eds.) Pergamon Press, Oxford]. Biotype A strains are of particular importance as the etiological agents of various types of gangrene and enteric diseases. A particularly serious enteric disease caused by *C. perfringens* is enteritis necroticans (also art-known as, "necrotic enteritis"), a gangrene of the intestines resulting in necrosis, sepsis, and hemolysis, in both humans and domesticated animals [see, Pearson et al., *J. Am. Vet. Med.* 188(11):1309-10 (1986); Al-Sheikhy and Truscott, *Avian Dis.* 21(2):256-63 (1977)]. For avians, e.g., chickens (*Gallus gallus*), enteritis necroticans is a significant problem. *C. perfringens* of either type A or type C can cause major losses, especially in production broiler chickens [Ficken and Wages, Necrotic Enteritis, In Diseases of Poultry, 10th Ed. pps 261-264 (1997)]. In addition to losses associated with necrotic enteritis outbreaks, productivity is reported to be impaired in flocks with *C. perfringens*-associated disease [Lovl and Kaldhusdal, *Avian Pathology* 30:73-81 (2001)]. As noted above, antibacterial agents inserted in the animal feed are the most common method of control. However, antibacterial agents, e.g., antibiotics, are costly and subject to increasing concerns related to the promotion of bacterial resistance.

More recently, attempts have been made to provide vaccines against harmful Clostridium species. For example, Lovland et al. [*Avian Pathology* 33(1):83-92 (2004)] demonstrated candidate vaccines based on *C. perfringens* type A and type C toxoids with an aluminum hydroxide adjuvant. Vaccination of parent hens was reported to provide specific antibodies to protect progeny against enteric lesions induced by subclinical challenge with *C. perfringens*. Other toxoid-based vaccines prepared from detoxified *C. perfringens* toxins are known [see e.g., U.S. Pat. No. 4,292,307, which describes toxoids of *C. perfringens* types A, B and D, *Cl. oedematiens*, and *Cl. septicum*].

Recombinant toxoid preparations also have been proposed. For example, Titball et al., [U.S. Pat. Nos. 5,851,827, 6,403,094, and 5,817,317] report nucleic acids that encode antigenic *C. perfringens* peptides, as well as the peptides themselves, and vaccines prepared from the peptides. Peptides are described for example, which have amino acid residues 261 to 300 of the natural *C. perfringens* alpha-toxin, but lack the phospholipase C and sphingmyelin hydrolyzing domains of the natural toxin. It was further reported that these peptides induce immune protection against the natural toxin. In addition, U.S. Pat. No. 6,610,300 describes a vaccine based on an antigenic fragment of a mutein *C. perfringens* beta-toxin.

However, no matter whether a toxoid vaccine is derived from the native organism or is obtained recombinantly, it is considered to be economically burdensome to produce and administer toxoid proteins to animals in need of immunization, except under special circumstances (e.g., treating humans who might be allergic or sensitive to other components of a whole organism vaccine). Further, protein/toxoid based-vaccines typically require repeated booster vaccinations in order to maintain full effectiveness.

Another proposed solution has been to engineer an antigenically active virus that will produce a mutein alpha-toxin, in place of the wild-type toxin. For example, Bennett et al. [*Viral Immunol.* 12(2):97-105 (1999)] have demonstrated a recombinant vaccinia virus vector that expresses a nontoxic C-domain of *C. perfringens* alpha-toxin. Unfortunately, while several recombinant vaccinia vaccines have been proposed during the past 20 years, there are still longstanding concerns about the safety of releasing live, infectious vaccinia viruses into an environment where they might be transmitted to those people who are not resistant to this virus.

The alpha-toxin (plc gene) of *C. perfringens* is known to possess several biological activities including hemolytic activity, phospholipase C, sphingomyelinase, phosphodiesterase, and lethal activities. There are a number of reports in the art concerning mutations to this alpha-toxin that reduce toxicity. Schoepe, et al. [*Infect. and Immun.* 69(11): 7194-7196 (2001)] describe a naturally-occurring *C. perfringens* strain that produces a non-toxic alpha-toxin. However, it would be difficult to modify this strain to elicit immune protection against other variant, but toxic wild-type *C. perfringens* species.

Williamson and Titball [*Vaccine* 11(12):1253-1258 (1993)] showed that the region of the toxin from amino acid residues 247 to 370 alone was sufficient to immunize mice against gas gangrene experimentally induced by *C. perfringens*. Alape-Girón et al. [*Eur. J. Biochem.* 267:5191-5197 (2000)] have reported that substitutions in Asp269, Asp336, Tyr275, Tyr307, and Tyr331 reduced alpha-toxin toxicity. Nagahama, et al. [*Infect. and Immun.* 65:3489-3492 (1997)] reported that replacement of Asp-56, Asp-130, or Glu-152 resulted in reduced alpha-toxin toxicity. Nagahama et al. [*J. Bacteriology* 177:1179-1185 (1995)] reported that substitution of the histidine at position 68 with a neutral amino acid, such as glycine, in the *C. perfringens* alpha-toxin resulted in a complete loss of hemolytic, phospholipase C, sphingomyelinase, and lethal activity of the mutein alpha-toxin. This single amino acid change was believed to inactivate one of the three zinc-binding domains of the protein. The zinc-binding domain inactivated by substitution of His68 was later denoted as Zn2 [Justin et al., *Biochemistry* 41:6253-6262 (2002)].

Despite the foregoing, there remains a need in the art for a safe, economical and effective method of protecting intensively cultivated domestic animals, including avians, such as chickens, from infection by *Clostridium* species, including *C. perfringens*.

The citation of any reference herein should not be construed as an admission that such reference is available as "prior art" to the instant application.

SUMMARY OF THE INVENTION

In order to address the above-described shortcomings in the art, the present invention provides nucleic acid molecules that encode a substantially nontoxic mutein of *Clostridium perfringens* alpha-toxin. In one such embodiment, the nucleic acid molecule encodes a mutein alpha-toxin that comprises the amino acid sequence of SEQ ID NO: 3, minus at least 18 consecutive amino acid residues, wherein one of the deleted amino acid residues is $His_{68}$. In another embodiment, the nucleic acid molecule encodes a mutein alpha-toxin that comprises the amino acid sequence of SEQ ID NO: 3, minus at least 12 consecutive amino acid residues, wherein one of the deleted amino acid residues is $His_{68}$. In still another embodiment, the nucleic acid molecule encodes a mutein that comprises the amino acid sequence of SEQ ID NO: 3 minus at least 9 consecutive amino acid residues, wherein one of the deleted amino acid residues is $His_{68}$. In yet another embodiment, the nucleic acid molecule encodes a mutein that comprises the amino acid sequence of SEQ ID NO: 3 minus at least 6 consecutive amino acid residues, wherein one of the deleted amino acid residues is $His_{68}$. In still another embodiment, the nucleic acid molecule encodes a mutein that comprises the amino acid sequence of SEQ ID NO: 3 minus at least 3 consecutive amino acid residues, wherein one of the deleted amino acid residues is $His_{68}$.

In one embodiment, a nucleic acid molecule of the present invention encodes a mutein in which no more than 48 consecutive amino acid residues are deleted from the amino acid sequence of SEQ ID NO: 3. In another embodiment, a nucleic acid molecule encodes a mutein in which no more than 36 consecutive amino acid residues are deleted from the amino acid sequence of SEQ ID NO: 3. In yet another embodiment a nucleic acid molecule encodes a mutein in which no more than 24 consecutive amino acid residues are deleted from the amino acid sequence of SEQ ID NO: 3. In still another embodiment a nucleic acid molecule of the present invention encodes a mutein in which no more than 18 consecutive amino acid residues are deleted from the amino acid sequence of SEQ ID NO: 3.

In a particular embodiment, the present invention provides a nucleic acid molecule encoding a mutein in which nine consecutive amino acid residues are deleted from the amino acid sequence of SEQ ID NO: 3, one of which is $His_{68}$. In a particular embodiment of this type, the nucleic acid molecule encodes a mutein in which the deleted nine consecutive amino acid residues range from $Tyr_{62}$ through $Trp_{70}$ of SEQ ID NO: 3. In a more particular embodiment, the nucleic acid molecule encodes a mutein in which these deleted nine consecutive amino acids are replaced by a single leucine residue.

In another embodiment, the nucleic acid molecule comprises the nucleotide sequence of SEQ ID NO: 2, wherein nucleotides 268-294 are deleted. In a specific embodiment of this type, nucleotides 268-294 of the nucleotide sequence of SEQ ID NO:2 are replaced by three nucleotides that encode a single leucine residue.

The invention also provides substantially nontoxic muteins of *Clostridium perfringens* alpha-toxin. In one such embodiment the mutein alpha-toxin comprises the amino acid sequence of SEQ ID NO: 3 minus at least 18 consecutive amino acid residues, wherein one of the deleted amino acid residues is $His_{68}$. In another embodiment, the mutein comprises the amino acid sequence of SEQ ID NO: 3 minus at least 12 consecutive amino acid residues, wherein one of the deleted amino acid residues is $His_{68}$. In still another embodiment, the mutein comprises the amino acid sequence of SEQ ID NO: 3 minus at least 9 consecutive amino acid residues, in which one of the deleted amino acid residues is $His_{68}$. In yet another embodiment, the mutein comprises the amino acid sequence of SEQ ID NO: 3 minus at least 6 consecutive amino acid residues, wherein one of the deleted amino acid residues is $His_{68}$. In still another embodiment, the mutein comprises the amino acid sequence of SEQ ID NO: 3 minus at least 3 consecutive amino acid residues, wherein one of the deleted amino acid residues is $His_{68}$.

In one embodiment, a mutein of the present invention comprises no more than 48 consecutive amino acid residues that are deleted from the amino acid sequence of SEQ ID NO: 3. In another embodiment, the mutein comprises no more than 36 consecutive amino acid residues deleted from the amino acid sequence of SEQ ID NO: 3. In yet another embodiment the mutein comprises no more than 24 consecutive amino acid residues deleted from the amino acid sequence of SEQ ID NO: 3. In still another embodiment the mutein comprises no more than 18 consecutive amino acid residues deleted from the amino acid sequence of SEQ ID NO: 3.

In a particular embodiment, the present invention provides a substantially nontoxic mutein in which nine consecutive amino acid residues are deleted from the amino acid sequence of SEQ ID NO: 3, one of which is $His_{68}$. In a more particular embodiment of this type, the deleted nine consecutive amino acid residues range from $Tyr_{62}$ through $Trp_{70}$ of SEQ ID NO: 3. In still a more particular embodiment, these deleted nine consecutive amino acids are replaced by a single leucine residue in the amino acid sequence of the mutein.

The invention further provides attenuated *Clostridium perfringens* organisms that have a nucleic acid molecule that encodes a substantially nontoxic mutein of *Clostridium perfringens* alpha-toxin integrated into their chromosomes. This integrated nucleic acid molecule is preferably located at a position on the chromosome that is homologous to the location of the nucleic acid molecule that encodes the wild-type alpha-toxin in the wild-type *Clostridium perfringens* organism. Thus, an attenuated *Clostridium perfringens* organism of the present invention can be substantially nontoxic due to the lack of a functional wild-type plc gene. As exemplified herein, the attenuated *Clostridium perfringens* organism can be a type A *Clostridium perfringens*.

In a particular embodiment of the present invention, the attenuated *Clostridium perfringens* organism is *Clostridium perfringens* CPERF/ΔαToxin 365-054 (ATCC Deposit No. PTA7364). In another particular embodiment of the present invention, the attenuated *Clostridium perfringens* organism is *Clostridium perfringens* CPERF/ΔαToxin 365-053 (ATCC Deposit No. PTA7365).

A *Clostridium perfringens* organism that is attenuated by the methods of the present invention can be isolated from a host animal that is either a mammal or an avian. Such mammals can include: bovine, ovine, and porcine. Examples of appropriate avians include chickens, turkeys, ducks, pigeons, geese, doves, swans, partridge, and grouse.

The present invention also provides vaccines. Such vaccines can comprise the attenuated *Clostridium perfringens* organisms of the present invention. The vaccines of the prevent invention can also include pharmacologically acceptable buffers, excipients, and/or adjuvants.

In addition, the invention provides methods of inducing immunity to *Clostridium perfringens* in an animal. One such embodiment comprises administering an immunologically effective dose of a vaccine of the present invention to the animal. The vaccines of the present invention can be administered by a number of routes including: orally, intramuscularly, intravenously, intradermally, subcutaneously and intranasally. A vaccine of the present invention can be top-dressed on the feed of the animal and/or sprayed onto the animals to provide for oral administration. The present invention further provides an animal feed that includes a vaccine of the present invention.

The present invention also provides an attenuated *Clostridium perfringens* organism of the present invention that in addition, expresses at least one gene encoding a non-*Clostridium perfringens* polypeptide. In one such embodiment one or more of the non-*Clostridium perfringens* polypeptides are bacterial polypeptides, such as antigenic proteins from *E. coli*, salmonella, lawsonia, or campylobacter etc., and/or combinations thereof. Alternatively, or in combination therewith, a non-*Clostridium perfringens* polypeptide can be a non-bacterial polypeptide. Examples of such non-bacterial polypeptides include mammalian or avian proteins, e.g. cytokines, such as chicken IL-18; viruses such as rotavirus or coronavirus; and parasites such as eimeria, isospora, and cryptosporidium.

In another aspect, the present invention provides an antibody that selectively binds to an epitope missing from the substantially nontoxic mutein of *Clostridium perfringens* alpha-toxin. Such antibodies can distinguish the substantially nontoxic mutein from a wild-type *Clostridium perfringens* alpha-toxin.

Test kits are also provided that include the antibodies of the present invention for use in identifying whether a subject animal has been vaccinated, or alternatively, has been naturally infected by a *Clostridium perfringens* organism.

Accordingly, methods of identifying and/or distinguishing an animal that has been naturally infected by a *Clostridium perfringens* organism from one vaccinated with an attenuated *Clostridium perfringens* organism are also provided. In one such embodiment the method entails contacting a fluid sample from the animal with an antibody that selectively binds to an epitope found in a wild type *Clostridium perfringens* alpha-toxin that has been deleted from the substantially nontoxic mutein of *Clostridium perfringens* alpha-toxin of the present invention. Therefore, the antibody can distinguish those animals that have been vaccinated with a substantially nontoxic mutein of *Clostridium perfringens* alpha-toxin of the present invention, (and/or an attenuated *Clostridium perfringens* organism expressing the mutein) from those that are infected or had been infected by a wild type *Clostridium perfringens* alpha-toxin. The next step is to determine whether the antibody reacts with the fluid sample, e.g., binds to an antigen contained by the fluid sample. The animal is identified as one that has/had been naturally infected by a *Clostridium perfringens* organism when the antibody reacts with the fluid sample.

BRIEF DESCRIPTION OF THE FIGURES

FIG. 2A illustrates the sequence of a portion of the plc gene from *C. perfringens* strain CP6 [SEQ ID NO: 4; this is a portion of SEQ ID NO: 22, (i.e., nucleotides 262-300) of a plc gene fragment from CP6] and the corresponding peptide sequence (SEQ ID NO: 5), where the underlining indicates the BamHI endonuclease restriction site used in creating the deletion.

FIG. 2B illustrates the sequence of the primer (SEQ ID NO: 6) used to create the deletion in the parent *C. perfringens* strain 1240, giving rise to the deletant CPERF001. The underlining indicates the BamHI restriction site included in the primer to facilitate construction of the deletion. Also illustrated is the corresponding peptide (SEQ ID NO: 7).

FIG. 2C illustrates the sequence of the resulting deletion in CPERF001 (SEQ ID NO: 8; nucleotides 103-117) and in the corresponding peptide (SEQ ID NO: 9). The underlining indicates the restored BamHI endonuclease restriction site.

FIG. 3A once again illustrates the sequence of a portion of the plc gene from *C. perfringens* strain CP6 [SEQ ID NO: 4, nucleotides 262-300] and the corresponding peptide sequence (SEQ ID NO: 5), where the underlining indicates the BamHI endonuclease restriction site used in creating the deletion.

FIG. 3B illustrates the sequence of the primer (SEQ ID NO:10) used to create the deletion in the parent *C. perfringens* strain 29, giving rise to the deletant CPERF002. Also illustrated is the corresponding peptide (SEQ ID NO:11).

FIG. 3C illustrates the sequence of the resulting deletion in CPERF002 (SEQ ID NO: 12) and corresponding peptide (SEQ ID NO: 13).

DETAILED DESCRIPTION OF THE INVENTION

Figure 1:
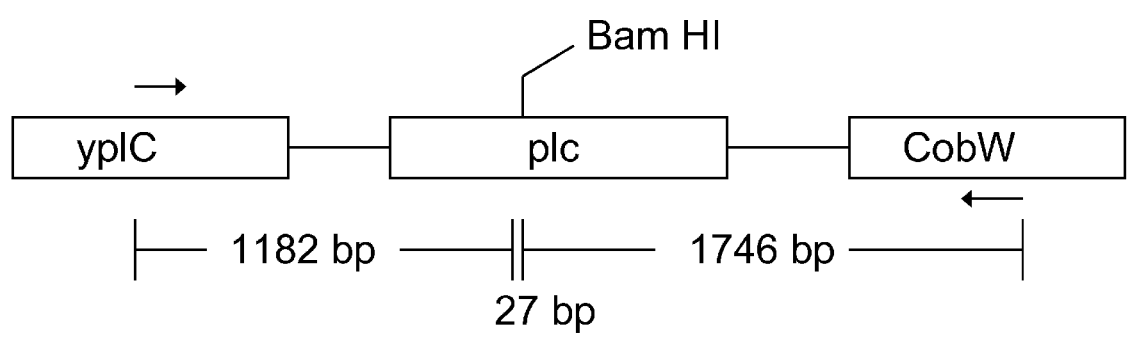
FIG. 1 illustrates a genomic map of the *C. perfringens* alpha-toxin encoding region. The locations of the two large (1182 base pair and 1746 base pair) fragments, respectively, that were used to construct CPERF001 are shown. The location of the resulting 27 base pair deletion is also indicated. "Yplc" indicates the yplc gene (CPE0035); "plc" indicates the gene encoding alpha-toxin (a phospholipase C), and "CobW" indicates a downstream gene.

Accordingly, the invention provides modified *Clostridia* organisms and cultures that express one or more of the *Clostridia* toxins, e.g., alpha-toxins, as muteins that have no detectable toxicity, and/or substantially low toxicity, relative to the native or wild-type *Clostridia* toxins. Advantageously, the inventive *C. perfringens* mutant organisms are readily administered as a live vaccine to animals. The inventive mutein *C. perfringens* alpha-toxins are also provided, together with nucleic acid molecules that encode the muteins, vectors for expressing the alpha-toxins, and methods of using the same.

In order to provide a clear description of the invention, several terms are defined, as follows. A vaccine is a composition that includes an immunogen, and other optional pharmaceutically acceptable ingredients, including, in certain embodiments, suitable adjuvants. As used herein, the term "immunogen" describes a composition, substance or vector, that when introduced into an animal, stimulates an immune response. For purposes of the present invention, an immunogen is contemplated to include any vector capable of expressing or introducing the inventive mutein alpha-toxin into an animal to be immunized. A vector includes, e.g., the inventive *C. perfringens* or other suitable microorganism, that expresses the inventive mutein alpha-toxin when the vector is introduced into an animal. A vector also includes art-known nucleic acid molecules, e.g., plasmids and the like, that express the inventive mutein alpha-toxin when directly introduced into an animal, e.g, by entering a cell of the animal and expressing the mutein alpha-toxin in the animal. An immunogen is also a protein, such as the inventive alpha-toxin, employed by itself or as part of a suitable vaccine composition.

As used herein, and unless otherwise specified, the terms "immunize" and "vaccinate" are synonymous and are used interchangeably to describe the introduction of an immunogen into an animal to elicit an immune response in the animal. The elicited immune response provides protective immunity to the treated animal that limits or reduces clinical disease signs, e.g., gas gangrene, and/or mortality, in vaccinated animals that are later challenged with a virulent dose of a *C. perfringens* species for which the inventive vaccine is protective.

The term "adjuvant" is defined as one or more substances that cause stimulation of the immune system. In this context, an adjuvant is used to enhance an immune response to one or more vaccine antigens/isolates. An adjuvant may be administered to the target animal before, in combination with, or after the administration of the vaccine. Adjuvants of the present invention may be obtained from any of a number of sources including from natural sources, recombinant sources, and/or be chemically synthesized, etc. Examples of chemical compounds used as adjuvants include, but are not limited to aluminum compounds; metabolizable and non-metabolizable oils; block polymers; ISCOM's (immune stimulating complexes); vitamins and minerals (including but not limited to: vitamin E, vitamin A, selenium, and vitamin B12); Quil A (saponins); crosslinked acrylic acid-based polymers (e.g., prop-2-enoic acid polymers) crosslinked to different levels with a polyalkenyl polyether, as sold under the trademark CARBOPOL®; and/or uniformly dispersed micron size oil droplets in water emulsion, e.g., as sold under the trademark Emulsigen®.

Additional examples of adjuvants, that sometimes have been referred to specifically as immune stimulants, include, bacterial and fungal cell wall components (e.g., lipopolysaccarides, lipoproteins, glycoproteins, muramylpeptides, beta-1,3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In addition, any number of combinations of the aforementioned substances may provide an adjuvant effect, and therefore, can form an adjuvant of the present invention.

The term "antibody" as used herein is intended to encompass polyclonal antibodies, monoclonal antibodies, and/or fragments or recombinant derivatives thereof, including engineered binding proteins incorporating antibody variable domains.

As used herein, the residue numbering and position of the amino acid residues of the inventive alpha-toxin proteins are based on the number system described for *Clostridium perfringens* strain 13. The *C. perfringens* strain 13 alpha-toxin is reported by GenBank Accession No. NC 003366 as illustrated by SEQ ID NO: 1. The entire protein is 398 amino acids long. The alpha-toxin encoded by the mutein vectors exemplified hereinbelow correspond to the protein of SEQ ID NO: 1 having a deletion of amino acid residues 90-98. There is a 28 amino acid signal sequence which is cleaved off during the maturation of the protein. Therefore the exemplified deletion corresponds to amino acid residues 62-70 of the mature protein, that is 370 amino acids in length (SEQ ID NO: 3).

The codon numbering of the DNA encoding the inventive alpha-toxin proteins is based upon the plc gene of *Clostridium perfringens* strain 13, as reported in GenBank Accession No. NP 560952, and as illustrated by SEQ ID NO: 2. The coding sequence for alpha-toxin runs from nucleotide 48590 through 49786 in *C. perfringens* strain 13. The codon deletion in the two constructs exemplified herein corresponds to nucleotides 48857 through (and including) 48883 of the NP 560952 gene. This deletion is found within the alpha-toxin gene and corresponds to nucleotides 268-294 in the coding sequence of SEQ ID NO: 2.

Further, the use of singular terms for convenience in the description is in no way intended to be so limiting. Thus, for example, reference to a composition comprising a *C. perfringens* cell includes reference to one or more of such cells. It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

In a particular aspect of the present invention, non-reverting mutants of *C. perfringens* are provided that are "substantially nontoxic," i.e., organisms that express an immunogenic alpha-toxin of little or no toxicity thereby rendering them suitable for use as protective vaccines. The inventive *C. perfringens* organisms therefore bestow a sufficiently reduced toxicity, relative to wild-type *C. perfringens* organisms, to render them tolerable as a vaccine or antigen, when employed under conditions effective to elicit an anti-alpha-toxin or anti-*C-perfringens*, immune response in an animal that is so vaccinated. Thus, the inventive *C. perfringens* organism is "attenuated" relative to the wild-type *C. perfringens*.

The phrase, "substantially nontoxic" is also intended to apply to the above-noted immunogenic alpha-toxin muteins that have sufficiently low or no toxicity, thereby also making them suitable for use in a protective vaccine.

The reduction in toxicity is measured, e.g., by one of the following art-known tests: hemolytic activity, phospholipase C activity, sphingomyelinase activity, phosphodiesterase activity, and general lethal activity in a test animal group. Generally, no residual toxicity is detectable by such standard tests. Nevertheless, the presence of a minimal level of one or more of these activities, e.g., from about $10^{-4}$ to about $10^{-2}$, relative to the toxicity of an equivalent number of infectious units of the wild-type *C. perfringens* alpha-toxin from which the mutein has been derived, may prove acceptable in a veterinary setting.

In a one embodiment, the invention is practiced employing biotype A strains of *C. perfringens*, which are of particular importance as the etiological agents of various types of gangrene and enteric diseases. In particular, the alpha-toxin of *C. perfringens* is the target for deletion-attenuation, since attenuation of this toxin is sufficient to render *C. perfringens* sufficiently non-lethal, relative to wild-type strains.

Broadly, the inventive *C. perfringens* plc gene expresses a mutein alpha-toxin. The mutein alpha-toxin has a deletion that includes the His of the Zn2 loop, together with flanking residues, in order to greatly reduce the possibility of any back mutation to the toxic form. It has now been found that deletion of the Zn2 loop His residue, e.g., $His_{68}$ of SEQ ID NO: 3, together with the deletion of additional residues flanking the His residue of the Zn2 loop, provides an alpha-toxin retaining sufficient immunogenicity to induce protective immunity in animals vaccinated with the inventive *C. perfringens*, while also being unlikely to undergo a back-mutation to encoding a wild-type alpha-toxin. The additional residues that can be deleted are deleted in the C-terminal direction and/or in the N-terminal direction, relative to $His_{68}$, and can range in number from about 4 through about 60 residues in either of those directions. Alternatively, $His_{148}$ and flanking residues, can be similarly deleted.

One embodiment of the inventive mutein alpha-toxin also includes, in addition to the deletion of $His_{68}$, a deletion of at least 30 amino acid residues from either side (in the C-terminal or N-terminal direction) of the $His_{68}$ position, relative to SEQ ID NO: 3. In another embodiment, the inventive mutein alpha-toxin includes, in addition to the deletion of $His_{68}$, a deletion of at least 20 amino acid residues from either side of $His_{68}$, relative to SEQ ID NO: 3. In still another alternative embodiment, the inventive mutein alpha-toxin includes, in addition to the deletion of $His_{68}$, a deletion of at least 5 amino acid residues from either side of $His_{68}$, relative to SEQ ID NO: 3. In yet another embodiment, the inventive mutein alpha-toxin includes a deletion from about residue 62 through about residue 70, relative to SEQ ID NO: 3. Optionally, the deleted amino acid residues are replaced by one or more other residues, such as a single leucine residue.

In still further another embodiment, the mutein *C. perfringens* alpha-toxin is produced and isolated from *C. perfringens*, or from an alternative recombinant organism, to be employed as a research reagent, and/or in diagnostic kits or assays, e.g., as a target for anti-alpha-toxin antibodies. Yet another utility for the mutein *C. perfringens* alpha-toxin proteins is in specialized vaccines for animals, e.g., humans, that may not tolerate vaccination with the inventive attenuated *C. perfringens* organism.

In addition, the present invention provides an antibody that specifically binds to the wild-type alpha-toxin relative to the alpha-toxin muteins of the present invention.

In a further embodiment, an antibody is provided that preferentially binds to wild-type *C. perfringens* alpha-toxin protein while exhibiting minimal or no binding to the inventive mutein alpha-toxin, e.g., avoiding binding to an alpha-toxin mutein that has a deletion as described in detail, supra. The antibody provided is therefore useful for distinguishing the deletion mutein alpha-toxin from the wild-type alpha-toxin, and thereby, also useful for distinguishing animals vaccinated with a vaccine of the present invention from animals that have been infected by wild type *C. perfringens*. Methods of eliciting and screening for such selective antibodies are art-known. Similarly, antibodies that recognize the inventive mutein alpha-toxin of the present invention, but not the wild-type protein can also be generated. The antibodies of the present invention can be polyclonal, monoclonal ("mAb") or fragments or engineered fragments or derivatives of such antibodies retaining selective binding properties.

Techniques for preparing and screening monoclonal antibodies have been amply described [see, e.g., Stites, et al. (eds.) *Basic and Clinical Immunology* (4th ed.), Lange Medical Publications, Los Altos, Calif. (1988); Harlow and Lane, *Antibodies: A Laboratory Manual*, CSH Press (1988); Goding, *Monoclonal Antibodies: Principles and Practice* (2d ed.), Academic Press, New York (1986); and Kohler and Milstein, *Nature* 256:495-497 (1975), all of which are incorporated by reference herein in their entireties].

For instance, and without limitation, an immune response is elicited in suitable animals, such as a mouse or chicken, by vaccination with a purified wild-type *C. perfringens* alpha-protein, e.g., in combination with a suitable adjuvant. For example, in order to avoid the toxicity of the wild-type alpha protein, the immunogen is a peptide corresponding to the deleted residues, and, if necessary the immunogenicity of the peptide is enhanced by combination with a suitable adjuvant or by coupling to a suitable carrier protein. Coupling to a carrier protein is art known, and can be accomplished, e.g., by providing the peptide with a terminal cysteine, and coupling it to keyhole limpet hemocyanin (KLH) or bovine serum albumin (BSA) using either maleimide coupling chemistry or sulfosuccinimidyl 4-[N maleimidomethyl]cyclohexane-1-carboxylate) linker (from Pierce) A carbodiimide linker also may be employed without requiring a terminal cysteine.

For preparation of monoclonal antibodies, splenic lymphocytes can be obtained from an immunized animal, hybridomas are prepared from those lymphocytes, and one or more potentially suitable hybridomas expressing anti-alpha protein can be obtained. The hybridomas are screened against both mutein and wild-type alpha-protein, and a hybridoma expressing an antibody that binds only to the wild-type alpha-toxin is identified, cloned and employed to produce monoclonal antibodies that bind only to the wild-type alpha protein. Optionally, cDNA from the identified hybridoma clonal line is obtained, and recombinant antibodies or antibody fragments can be produced in other art-known expression systems.

As discussed above, one potential disadvantage of vaccinations in general is that the resulting vaccinated animals can generate false positives when testing for infection using antibodies raised against a naturally occurring strain, thereby, hindering the identification of infected animals. Therefore, the present invention provides a test kit for distinguishing a subject animal that has been infected by a naturally occurring *C. perfringens* organism from one vaccinated with a mutein alpha-toxin of the present invention.

One such test kit includes a quantity of a selective anti-wild-type alpha-toxin antibody that exhibits minimal or no binding to a mutein alpha-toxin of the present invention. The kit can also include other suitable reagents, sufficient for conducting at least one diagnostic test. In a further embodiment, the antibody is tagged or labeled with a readily detectable maker moiety, e.g., any art-known enzymatic marker, e.g., peroxidase; fluorescent tag, e.g., fluorescein; beads, including magnetic beads; and the like. Optionally, the kit can further include a tagged antibody that selectively binds to the selective anti-wild-type alpha-toxin antibody. Immunoassays are well known to the art, and include sandwich immunoassay, competitive immunoassays, enzyme-linked immunosorbent assays (ELISA), radioimmunoassays (RIA) and others.

Also provided are methods for identifying and distinguishing an animal that has been infected by a naturally occurring, i.e., wild-type, *C. perfringens* organism, from an animal vaccinated with a vaccine comprising the attenuated *C. perfringens* organism of the invention, that is conducted, for example, by the following steps:

(a) contacting a fluid sample from the animal with an above-described selective anti-wild-type alpha-toxin antibody that exhibits minimal or no binding to a mutein alpha-toxin of the present invention; and (b) determining whether the antibody reacts with the fluid sample; wherein when the antibody reacts with the fluid sample, the animal is identified as one that has been infected by a naturally occurring *C. perfringens* organism.

Producing Attenuated *C. Perfringens* Strains

A process of converting a wild-type *C. perfringens* isolate into an attenuated, or substantially nontoxic, strain suitable to be administered as a vaccine can be conducted as follows. The alpha-toxin (plc) gene can be replaced on the bacterial chromosome with a gene encoding only an alpha-toxin mutein, leaving no remaining capability for the *C. perfringens* organism to produce wild-type alpha-toxin. Very broadly, the process of producing the vaccine organism includes, but is not limited to, the following general steps, not necessarily in the order presented.

(1) Identifying the type of animal to be protected by vaccination and one or more clinical isolates obtained for screening purposes. This step is typically optional in the case for the alpha-toxin, since isolates from one species of animal are more likely than not to provide protection for other species of animal.

(2) Amplifying the plc gene from the *C. perfringens* isolate or isolates, e.g., by PCR or other art-known nucleic acid amplification technique, with suitable flanking primers, and employing amplification with suitable primers to create the desired deletion mutation. Alternatively, an appropriate library can be probed.

(3) Creating a suicide vector comprising the deletion plc gene, in which the *C. perfringens* origin of replication has been removed, and/or an origin of replication that can replicate in *C. perfringens* is simply not present; and in either case, including suitable selectable markers, e.g., antibiotic markers, adjacent to the mutated plc gene. Such a vector can then be inserted into *C. perfringens* organisms, e.g., by electroporation, or other art-known methods.

(4) Selecting *C. perfringens* organisms in which the mutein plc gene has been successfully integrated into the bacterial chromosome. This is done by culturing the *C. perfringens* organisms of step (3) in the presence of the selectable agent, e.g., an antibiotic(s) corresponding to the selectable markers. For example, the only *C. perfringens* organisms that would grow under antibiotic selection would be those that through homologous recombination have directly integrated the suicide vector, with its antibiotic resistance gene(s), into the bacterial chromosome. These growing *C. perfringens* organisms therefore, would have two adjacent plc genes, one being wild-type, whereas the other would have the deletion mutation.

(5) Selecting *C. perfringens* organisms that have undergone a further recombination event that removes the selectable markers, e.g., antibiotic markers, along with the wild-type plc gene. This is done by culturing the organisms of (4) in the absence of the selectable agent, e.g., the antibiotic, and selecting for non-hemolytic clones on blood agar.

Since the insertion of the mutein nucleic acid is accomplished by homologous recombination, the nucleic acid molecule encoding the mutein alpha-toxin is incorporated at a chromosomal position that is homologous to the location of a nucleic acid molecule encoding a wild-type alpha-toxin that is present in non-attenuated *Clostridium perfringens*.

In more detail, field isolates of *C. perfringens* are obtained from diseased animals or other sources. Initially, genomic DNA obtained from field isolates of interest is inserted into a suitable dual microorganism shuttle vector, e.g., a shuttle plasmid with selectable markers, e.g., antibiotic markers, to assess their transformability. Broadly, a suitable shuttle vector will include one, two, three or more of the following features, a cloning site, a *C. perfringens* origin of replication, an *E. Coli* origin of replication, and an antibiotic resistance gene andor selectable marker. Art-known vectors suitable for this purpose, or readily adaptable for this purpose include, for example, the recombinant shuttle plasmid pHR106 described by Roberts et al., [*Appl Env Mircobiol* 54: 268-270 (1988)]; the PJIR 750 and PJIR 751 plasmids described by Bannam, et al., [*Plasmid* 29:233-235 (1993)]; the promoterless PPSV promoter selection vector of Matsushita, et al., 1994, *Plasmid* 31, 317-319; the shuttle plasmids pJIR1456 and pJIR1457, described by Lyras, et al., 1988, *Plasmid* 39, 160-164; and the pAK201 shuttle vector described by Kim et al., 1989, *Appl Environ Microbiol* 55, 360-365, the contents of which are incorporated herein by reference in their entireties. Removal of the *C. perfringens* origin of replication converts the shuttle vector into a suicide vector.

For example, one shuttle plasmid is pJIR418, described by Sloan, et al., 1992, *Plasmid* 27, 207-219, incorporated by reference herein.

Isolates yielding >104 transformants per microgram of plasmid DNA, and that are susceptible to the antibiotic marker, e.g., chloramphenicol or erythromycin, are potential candidates for deletion. Genomic DNA from the candidate strains is then used as a template for long range PCR of the plc (alpha-toxin) gene and flanking sequences of the candidate strains. For example, as exemplified hereinbelow, the *C. perfringens* strain 13 chromosome was used to identify primers for amplifying the gene encoding the alpha-toxin. These primers were then used to clone the alpha-toxin gene from another strain, that was the CP6 poultry isolate.

After subcloning of the PCR products, the alpha-toxin gene and flanking regions are sequenced and restriction mapped. New oligonucleotide primers are synthesized with flanking restriction sites and the products of two separate amplifications are cloned into a suitable suicide plasmid (*C. perfringens* origin of replication has been removed), e.g., exemplified hereinbelow as plasmid 1192-23.1 to create the desired vaccine strain with the deletion.

The provided suicide vector(s) specific to the isolate(s) are inserted into the corresponding animal strain of *C. perfringens*, by any standard art-known method. For example, this is accomplished by electroporation. When the suicide vector is inserted into *C. perfringens* (without the *C. perfringens* origin of replication, it is unable to replicate in the cytoplasm, and does not survive unless it successfully integrates into the bacterial chromosome.) Successful integrants are the only organisms that will grow in the presence of the antibiotic corresponding to the newly introduced antibiotic marker gene.

Any art-known selectable marker gene may be employed, although choramphenicol and/or erythromycin markers are employed in the vectors exemplified hereinbelow.

These recombinant events result from homology of the wild-type plc gene to the deletion plc gene plasmid DNA. The resulting recombinant bacteria is termed an integrant. The integrant contains a copy of the introduced homology vector that is integrated at the plc gene locus. Thus, the resulting integrant includes two copies of the plc gene, the original normal copy, and the introduced deleted version. The introduced antibiotic resistance genes are located between the two copies of the plc gene. Rare random recombination events can occur between the two copies of the plc gene. This recombination event can produce one of two outcomes. In both cases, the DNA intervening between the two copies of the plc gene (including the resistance genes) has been removed. In the first outcome, the normal or wild-type plc gene is restored, resulting in recovery of the original parent strain without antibiotic markers. In the second outcome, the wild-type plc gene is replaced by the deleted copy, producing the desired alpha-toxin deletant construct, without the antibiotic markers.

Removing the antibiotic from the culture medium allows those bacteria that have undergone recombination to survive and replicate. The deletion recombinant clones are then identified by growth on blood agar, without the hemolysis normally exhibited by *C. perfringens* that expresses the wild-type alpha-toxin.

Animals to be Vaccinated

Animals for which an attenuated *C. perfringens* vaccine can be produced, and from which a useful *C. perfringens* wild-type strain may be isolated, include, broadly, any animals for which *C. perfringens* infection is a problem. Vertebrates of interest include avians, mammals, and fish, and particularly animals of economic and/or agricultural importance. The following list of animals are those that are contemplated to benefit from a *C. perfringens* vaccine and/or from which useful *C. perfringens* wild-type isolates may be obtained. While it is sometimes possible that any such vaccine comprise a component (living or non-living) that was originally isolated from the same genus or species of animal that is to be vaccinated, this is not a requirement.

A non-limiting list of such animals include those of the avian, bovine, ovine, etc., families, as well as aquatic animals, e.g., that may be subjected to aquaculture and/or harvested from the wild and kept alive in holding tanks for a time prior to marketing. These include fish such as trout or salmon, and other species raised or harvested for economic benefit. Non-vertebrate aquatic animals include lobsters, crabs, mollusks, e.g., squid, octopus, clams, oysters, muscles, scallops, and the like. Avian shall be understood to include, for example, chickens, turkeys, geese, duck, etc. Bovine shall be understood to include, for example, cattle, beef, veal, etc. Ovine shall be understood to include, for example, lamb, etc.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp).

| TAXON NAME | COMMON NAME |
|---|---|
| *Salmonidae* Family | |
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta X S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus leucomaenis* | Japanese charr (white spotted charr) |
| *Salvelinus malma* | Dolly varden (Miyabe charr) |
| *Salvelinus namaycush* | Lake trout |
| *Thymallus thymallus* | Grayling |

| TAXON NAME | COMMON NAME |
|---|---|
| Some Members of the *Serranidae* Family | |
| *Centropristis ocyurus* | Bank sea bass |
| *Centropristis philadelphicus* | Rock sea bass |
| *Centropristis striata* | Black sea bass |
| *Diplectrum bivittatum* | Dwarf sandperch |
| *Diplectrum formosum* | Sand perch |
| *Epinephelus flavolimbatus* | Yellowedge grouper |
| *Epinephelus morio* | Red grouper |
| *Serranus phoebe* | Tattler |
| *Serranus tortugarum* | Chalk bass |
| Some Members of the *Sparidae* family | |
| *Archosargus probatocephalus* | Sheepshead |
| *Archosarpus rhomboidalis* | Sea bream |
| *Calamus penna* | Sheepshead porgy |
| *Lagodon rhomboides* | Pinfish |
| *Pagrus Major* | Red Sea bream |
| *Sparus aurata* | Gilthead Sea bream |
| *Stenotomus chrysops* | Scup |
| Some Members of the *Cichlidae* family | |
| *Aepuidens latifrons* | Blue acara |
| *Cichilsoma nigrofasciatum* | Congo cichlid |
| *Crenichichla* sp. | Pike cichlid |
| *Pterophyllum scalare* | Angel fish |
| *Tilapia mossambica* | Mozambique mouth breeder |
| *Oreochromis* spp | Tilapia |
| *Sarotherodon aurea* | Golden Tilapia |
| Some Members of the *Centrarchidae* family | |
| *Ambloplites rupestris* | Rock bass |
| *Centrarchus macropterus* | Flier |
| *Elassoma evergladei* | Everglades pigmy sunfish |
| *Elassoma okefenokee* | Okefenokee pigmy sunfish |
| *Elassoma zonatum* | Banded pigmy sunfish |
| *Enneacanthus gloriosus* | Bluespotted sunfish |
| *Enneacanthus obesus* | Banded sunfish |
| *Lepomis auritus* | Red breast sunfish |
| *Lenomis cyanellus* | Green sunfish |
| *Lepomis cyanellus* X *L. gibbosus* | Green x pumpkinseed |
| *Lepomis gibbosus* | Pumpkinseed |
| *Lepomis gulosus* | Warmouth |
| *Lepomis humilis* | Orange-spotted sunfish |
| *Lepomis macrochirus* | Bluegill |
| *Lepomis megalotis* | Longear sunfish |
| *Micropterus coosae* | Shoal bass |
| *Micropterus dolomieui* | Small mouth bass |
| *Micropterus punctulatus* | Spotted bass |
| *Micropterus salmoides* | Largemouth bass |
| *Pomoxis annularis* | White crappie |
| *Pomoxis nigromaculatus* | Black crappie |

In a further embodiment, the animal is a companion animal or a human. For purposes of the present invention, the term "companion" animal shall be understood to include all animals—horses (equine), cats (feline), dogs (canine), and rodents, including mice, rats, guinea pigs, rabbit species, and avians, such as pigeons, parrots, and the like.

Birds receiving such vaccination can be associated with either commercial or noncommercial aviculture. These include e.g., Anatidae, such as swans, geese, and ducks, Columbidae, e.g., doves and pigeons, such as domestic pigeons, Phasianidae, e.g., partridge, grouse and turkeys, Thesienidae, e.g, domestic chickens, Psittacines, e.g., parakeets, macaws, and parrots, e.g., raised for the pet or collector market. Chickens are exemplified hereinbelow.

Sources of Wild-Type Isolates

Generally, the attenuated *C. perfringens* organisms of the invention can be produced starting with a wild-type *C. per-*

*fringens* that has originally been isolated from any infected animal of interest, as discussed supra, and/or from the environment. The environment includes any material that contains viable *C. perfringens* organisms and/or viable *C. perfringens* spores including, for example, contaminated food, soil, water, animal bedding material, feces, and the like.

Justin et al., [*Biochemistry* 41, 6253-6262 (2002)] characterized alpha-toxins from different strains of *C. perfringens* that are almost identical in sequence and biochemical properties. However, Justin et al., also describe a strain that was isolated from an avian source (a swan) that had an alpha-toxin exhibiting a large degree of sequence variation and altered substrate specificity compared to the other strains. For this reason, it is believed that most isolates will, when converted to an attenuated form, elicit protective immunity against the alpha-toxin of many other naturally occurring strains of *C. perfringens*. Nevertheless, given the possibility of alpha-toxin variation between isolates, it will often be advantageous to isolate and attenuate *C. perfringens* organisms from the animal species for which an anti-*C. perfringens* vaccine is desired. The isolate exemplified hereinbelow was isolated from chicken, and tested in that species.

Vaccines

The attenuated *C. perfringens* organisms of the invention are generally formulated into pharmaceutically acceptable vaccine compositions. The vaccine compositions are formulated according to the route of administration and are compatible with the active antigenic agent. The active antigenic agent is, for example, one or more strains of attenuated *C. perfringens* type A organisms according to the invention. Optionally, the vaccine composition can also include one or more types of non-toxic alpha-protein, in combination with the attenuated *C. perfringens* type A organisms.

For example, substantially all of the attenuated *C. perfringens* type A organisms included in the vaccine composition are alive and viable, although for certain specific situations, e.g., for immunizing certain humans or immune-compromised animals, the vaccine will exclusively comprise killed attenuated *C. perfringens* type A organisms.

The vaccine composition includes physiologically compatible buffers and/or salts, in optional combination with adjuvants and/or optional immune enhancers or stimulants (co-administered or administered in series, e.g., before or after vaccination).

Suitable immune stimulants include, but are not limited to, cytokines, growth factors, chemokines, supernatants from cell cultures of lymphocytes, monocytes, cells from lymphoid organs, cell preparations or cell extracts (e.g. *Staphylococcus aureus* or lipopolysaccharide preparations), mitogens, or adjuvants including low molecular weight pharmaceuticals. An immune stimulant can be administered in ovo at any time during incubation. In a particular aspect, the immune stimulant is administered in the medium containing the attenuated *C. perfringens* type A organisms.

Methods of Administering Vaccine

The above-described inventive vaccines are administered, for example, by injection or inoculation by one or a combination of the following routes: oral, intranasal, parenteral, subcutaneous, scarification, and/on intramuscular administration in any suitable, art-known formulation, e.g., a compatible buffer and/or a physiologically acceptable saline, in optional combination with adjuvants and/or immune enhancers or stimulants (co-administered or administered in series, e.g., before or after vaccination). For orally-administered vaccines/vaccination methods, any of the physiologically-suitable buffers or suspending agents that are known to the art are readily employed. In addition, the composition can be incorporated, e.g., admixed into drinking water or sprayed onto food pellets, dusted or sprayed onto corn or other grains, and the like.

The gastrointestinal tract is a common site of *C. perfringens* infection, and therefore oral administration is contemplated as one method of inoculation. The presence of the gastrointestinal tract by the live attenuated *C. perfringens* organisms of the invention is contemplated to elicit localized protective immune reactions in the mucosal layer of the gastrointestinal tract, and may also act competitively to prevent subsequent colonization by wild-type *C. perfringens*.

For avians, such as domestic fowl, including chickens, ducks, geese, etc., the oral method, or injection in ovo are among the useful routes for vaccination. The in ovo route is exemplified hereinbelow, and produced active immunization and protection from challenge in the hatched chickens.

Foreign Gene Expression by *C. Perfringens*

Using the techniques developed in the preceding examples, any gene not naturally occurring, i.e., foreign to *C. Perfringens* optionally can be inserted into the chromosomal DNA of *C. perfringens*. For expression of foreign proteins, gene fusions can be made which preserve the sequences flanking the alpha-toxin gene, the alpha-toxin promoter and its signal sequence. In one embodiment, most of the coding sequence of the plc gene is replaced with the foreign gene. The remaining nucleotides of the plc gene downstream of the inserted gene are out of frame, and therefore no functional alpha-toxin is produced. Alternatively, the foreign gene can be inserted in-frame to the nucleotide sequence encoding the alpha-toxin mutein forming an alpha-toxin—foreign protein fusion protein.

Oligonucleotide primers for the foreign gene can be synthesized, e.g., with an N-terminal FLAG tag sequence and appropriate restriction sites. The PCR products can be cloned into the suicide vector; the FLAG tag and foreign gene are inserted in frame with the alpha-toxin signal sequence. The foreign protein is expressed under control of the alpha-toxin promoter and targeted for secretion by the plc signal sequence. The secreted foreign protein can be detected in the supernatant media by Western blot using an anti-FLAG antibody.

Any suitable foreign gene may be inserted into the *C. perfringens* genome in this manner. These include, for example, DNA encoding antigens from pathogens of the gastrointestinal tract, including, e.g., antigenic proteins of bacteria such as *E. coli*, *salmonella* species, *campylobacter* species, *lawsonia* species, and the like; antigenic proteins of parasites such as eimeria species, isospora species, cryptosporidium species and the like; and antigenic proteins of viruses such as *rotaviruses, coronaviruses*, and the like, in order to immunize the animal treated with such a recombinant *C. perfringens*. Other proteins that may be expressed by such recombinant *C. perfringens* include therapeutic proteins or peptides. Optionally, these include peptides that are endogenous to the gastrointestinal tract, including trefoil factor, or any type of art-known cytokine, e.g. chicken IL-18, and the like.

One such *C. perfringens* construct expresses the chicken IL-18 protein. Administration of live bacteria containing the gene fusion will allow delivery of therapeutic doses of IL-18 into the gut yet be relatively innocuous to the host animal by virtue of the absence of alpha-toxin production. Other therapeutic agents may also be expressed using this system.

Numerous references are cited herein, the content of each of which is incorporated by reference herein in its entirety. The following specific examples are included for purposes of illustration, and are not intended to limit the scope of the invention, unless otherwise indicated.

EXAMPLE 1

C. Perfringens Alpha-Toxin Deletant Homology Vector

A homology plasmid vector 1162-55-20 useful in the construction of *C. perfringens* alpha-toxin deletants was created. The plasmid incorporates several important elements; the replication region from the *E. coli* plasmid pUC1 8; the *C. perfringens* chloramphenicol (catP) and erythromycin (ermBP) resistance genes (both of which are also expressed in *E. coli*); and a *C. perfringens* alpha-toxin gene (plc) inactivated by a specific deletion of 9 amino acids. Plasmid 1162-55-20 was created in several steps, as follows.

First the plc gene was cloned from a recent avian isolate of *C. perfringens* (strain CP6). The sequence of *C. perfringens* strain 13 (Genbank NC 003366; SEQ ID NO: 2) was used to design oligonucleotide primers to be used in the cloning of the plc gene. These and all subsequent primers were obtained commercially form Sigma Genosys, Woodlands, Tex. The upstream primer located within the yplc gene (CPE0035), 5' AGCTGCATAAGCAAAAGTTCCAACTC 3' (SEQ ID NO: 14) corresponds to nucleotides 47675-47700 of strain 13 (SEQ ID NO: 2). The downstream primer located within the cobwgene (CPE0037), 5' GCAGAAACTCTTCTTAGAC-CTATTCTTTTAGGC 3' (SEQ ID NO: 15), is complementary to nucleotides 50597-50629 of strain 13. These primers were used along with genomic DNA from *C. perfringens* strain CP6 in a long range polymerase chain reaction (PCR). A product of 2955 base pairs from the upstream yplc gene through the downstream cob W gene was predicted from the known sequence of strain 13 (as illustrated by FIG. 1). The alpha-toxin promoter, signal sequence and plc gene (CPE0036) coding sequence are contained within this fragment, i.e. between the upstream yplc gene and the downstream cob W gene. The PCR 2955 base pair fragment was then cloned into cloning vector pCR-Blunt (Invitrogen Corporation, Carlsbad, Calif.) resulting in plasmid 1162-52.1. The nucleotide sequence of the plc coding region of the 2955 base pair fragment of strain CP 6, was determined from this fragment (SEQ ID NO: 22; and corresponding polypeptide is SEQ ID NO: 23) and was shown to be substantially homologous as that of the plc gene of *C. perfringens* strain 13 (SEQ ID NO: 2).

Next the *E. coli* replication region and the *C. perfringens* resistance genes were cloned from shuttle plasmid pJIR418 (Sloan, et al, 1992, *Plasmid* 27, 207-219; Genebank M77169). Plasmid pJIR418 was digested with restriction enzymes Bam HI and Spe I and the ends filled in with Klenow polymerase. Ligation of the large fragment produced plasmid 1162-45.1 and restored the Bam HI restriction site. This plasmid retains the *E. coli* replication region, but unlike pJIR418, it does not contain a *C. perfringens* origin of replication. The plasmid is therefore capable of autonomous replication in *E. coli*, but not in *C. perfringens*.

In the next step the C-terminal half of the plc gene was sub-cloned into the intermediate plasmid 1162-45.1. Digestion of plasmid 1162-52.1 with Bam HI and Eco RI released a 1742 base pair fragment containing the C-terminal portion of the alpha-toxin gene from the unique Bam HI site located with in the plc gene downstream through the cob W gene to an Eco RI site located in the multiple cloning site of the parent plasmid. The 1742 base pair fragment was cloned between the Bam HI and Eco RI sites located within the multiple cloning site of plasmid 1162-45.1. In the resulting plasmid 1162-53.7, the C-terminal half of the plc gene is in the same transcriptional orientation as the catP and ermBP genes of the parental plasmid.

In the final step the N-terminal half of the plc gene was cloned into the unique Bam HI site of plasmid 1162-53.7. This was accomplished by creating a PCR fragment derived from the alpha-toxin gene sub-cloned in plasmid 1162-52.1. The upstream primer, 5' ggatccAGCTGCATAAG-CAAAAGTTCCAACTC 3' (SEQ ID NO: 16) was identical to the previously noted yplc primer (SEQ ID NO: 4) except that a flanking Bam HI site (lowercase) was included. The downstream primer located within the alpha-toxin gene, 5' ggatccaATGCATTCTTATCATAATCTG-GATAAGTAGAACC 3' (SEQ ID NO: 17) was complementary to nucleotides 48824-48857 of strain 13 and included a flanking Bam HI restriction site and a spacer nucleotide to maintain the reading frame (lowercase). The Bam HI fragment resulting from PCR with these primers and plasmid 1162-52-1 template DNA was cloned into the unique Bam HI site of plasmid 1162-53.7. A plasmid containing the two plc gene regions in the same transcriptional orientation was isolated. This plasmid 1162-55.20 contains the plc gene with the desired nine amino acid deletion and the addition of a leu residue between the ala 61 and asp 71 of the wild-type toxin (see FIG. 2). DNA sequencing of the plasmid confirmed the reading frame and the net deletion of 24 codons (encoding eight amino acid residues).

EXAMPLE 2

Construction of *Clostridium Perfringens* Recombinant CPERF001

The deleted version of the plc gene constructed in Example 1 was introduced into *C. perfringens* using the following strategy. The homology vector 1162-55.20 is termed a *C. perfringens* "suicide plasmid" because its *C. perfringens* origin of replication has been removed.

When this plasmid was transformed into *C. perfringens* it is unable to replicate and does not survive. However, if the transformed bacteria are placed under chormaphenicol and/or erythromycin selection, the plasmid DNA can be forced to recombine into the bacterial genome via homology to the plc gene. The resulting recombinant bacteria is termed an integrant. The integrant contained a copy of the introduced homology vector that was the plc gene locus. Thus, the resulting integrant contained two copies of the original normal copy, and the introduced deleted version. The introduced resistance genes were located between the two copies of the plc gene. When antibiotic selection was removed from the integrant, recombination occurred between the two copies of the plc gene. This recombination event can produce one of two outcomes. In both cases, the DNA intervening between the two copies of the plc gene (including the resistance genes) has been removed. In the first outcome, the normal plc gene was restored, resulting in recovery of the original parent strain. In the second outcome, the normal plc gene is replaced by the deleted copy, producing the desired alpha-toxin deletant construct. Since the alpha-toxin of the deletant strain is inactivated, this strain was non-hemolytic. Therefore the desired deletant integrant was identified by screening for non-hemolytic clones on blood agar plates.

Because the recombination event resulting in the desired integrant was expected to occur at a low frequency, it was critical to employ parent *C. perfringens* strains having high transformation efficiency. Therefore several recent avian isolates of *C. perfringens* were analyzed for transformation efficiency. The isolates were transformed with the shuttle plasmid pJIR418 as described by Allen and Blaschek (*Applied and Environmental Microbiology* 54:2322 1988)) with slight modifications (described below). Strain 1240 exhibited the highest transformation efficiency (see Table 1), $9.2 \times 10^6$ transformants/μg of pJIR418 plasmid DNA. This strain was chosen to be the parent strain for construction of deletant CPERF001. Strain 29 was chosen to be the parent strain for CPERF002.

TABLE 1

Transformation Efficiency of *C. perfringens* Avian Isolates

| C. perf. A Strain | Transformants/μg of pJIR418 |
|---|---|
| 29 | $3.6 \times 10^4$ |
| 23 | $5.6 \times 10^2$ |
| 1220 | $4.0 \times 10^6$ |
| 1240 | $9.2 \times 10^6$ |
| CP-2 | None |
| 1230 | $7.1 \times 10^3$ |
| 5227 | None |
| 5230 | None |

Source of above listed wild-type strains was Dr. J. Glenn Songer, Dept. of Veterinary Sciences and Microbiology, University of Arizona, Tucson, Arizona 85721

*C. perfringens* strain 1240 cells from an overnight anaerobic culture in TSYC media (30 g/l tryptic soy broth, 5 g/l yeast extract, 0.5 g/l cysteine) were diluted 1:25 and grown to $A_{600}=0.5436$. After centrifugation of 100 ml of cells at 18,000×g for 10 minutes, electrocompetent cells were prepared by twice resuspending cells in an equal volume of pre-reduced sucrose magnesium phosphate ("SMP" was prepared as 270 mM sucrose, 1 mM $MgCl_2$, 7 mM $NaPO_4$, pH 7.3) buffer followed by a final resuspension with 0.5 ml SMP. This resulted in a final volume of ~2.0 ml.

Aliquots of 100 μl of cells were electroporated with 4 μg of plasmid 1162-55.20 in 0.2 cm cuvettes. A Bio-Rad Gene Pulser II was used at 1.37 kilovolts, 100 Ohms resistance and 50 microfarads capacitance. Immediately after electroporation, cells were diluted with 2.0 ml of pre-reduced tryptic soy yeast cysteine media ("TSYC" was prepared as 30 g tryptic soy broth, 5 g yeast extract, 0.5 g cysteine, 950 ml water) and incubated for three hours at 37° C. in an anaerobic jar. After the recovery period, dilutions of cells were plated on TSYC +25 μg/ml of chloramphenicol plates. These plates were incubated at 37° C. overnight in an anaerobic jar.

After overnight growth, an average of 50 chloramphenicol-resistant colonies per microgram of 1162-55.20 DNA was observed. Single colonies of seven putative integrants were grown up in nonselective TSYC media for four successive grow outs and plated onto nonselective blood agar plates. One of the non-selected stocks, 1192-31.7, exhibited several non-hemolytic colonies. Twenty-one of these non-hemolytic colonies were patched to nonselective master plates and replica plated on TSYC+chloramphenicol plates. Two of the 21 colonies were chloramphenicol sensitive.

One of the chloramphenicol-sensitive putative deletants, 1192-32.14, was grown up along with the 1240 wild-type and the integrant 1192-31.7 and plated on blood agar plates. The 1240 wild-type strain showed clear zones of beta hemolysis whereas the 1192-32.14 deletant was a pure culture of non-hemolytic colonies and was renamed CPERF001.

Other blood plates were used as masters and replica plated to nonselective and selective media. The 1240 wild-type and CPERF001 were chloramphenicol and erythromycin sensitive. The integrant, 1192-31.7, was both chloramphenicol and erythromycin resistant as expected.

To rule out the possibility that the antibiotic resistance genes were present but not expressed in CPERF001, PCR primers specific for the chloramphenicol and erythromycin genes were synthesized for use in PCR reactions. Genomic DNAs were prepared from the wild-type, integrant and CPERF001 strains and used as templates for PCR reactions with the antibiotic gene primers. Results of the PCR analysis showed positive response only from the suicide plasmid and the integrant and not the parent 1240 or deletant CPERF001. This confirms the predicted loss of the resistance gene sequences.

To confirm the deletion within the alpha-toxin gene, a 1086 bp region surrounding the deletion was amplified by PCR using appropriate alpha-toxin specific primers. The amplified fragment was cloned and sequenced. Sequencing results confirmed the deletion of the nine amino acids from tyr 62 through trp 70 of the alpha-toxin gene and the insertion of a single leu (see FIGS. 2A-2C).

CPERF001 was assayed for expression of the inactivated alpha toxoid protein. After 6 hours of anaerobic growth, aliquots of 1 ml of cells were collected and centrifuged. Fifteen microliters of the unconcentrated supernatant media were analyzed by polyacrylamide gel electrophoresis and subjected to Western Blot analysis with a rabbit polyclonal antibody directed against recombinant alpha-toxin protein (Vaccine 11(12): 1253-1258 (1993)). The results showed specific antibody reactivity with a protein of the expected size for the alpha toxoid protein.

CPERF001 is a genetically engineered deletant strain of *C. perfringens* Type A. This strain secretes an inactivated toxoid form of the *C. perfringens* alpha-toxin. Because this strain no longer expresses active alpha-toxin yet retains a significant portion of the toxin's antigenicity, it will be useful as a vaccine to protect against disease caused by *C. perfringens*.

EXAMPLE 3

Construction of *Clostridium Perfringens* Recombinant CPERF002

In order to compensate for the lower transformation efficiency of *C. perfringens* strain 29 (see Table 1, supra) a new homology vector was constructed. The new vector incorporated *C. perfringens* sequences cloned directly from the strain 29 genome. This was predicted to result in a more efficient recombination step. The new vector was 1192-38.3 created as follows.

In the first step the *E. coli* replication region and the *C. perfringens* resistance genes were cloned from shuttle plasmid pJIR418 (Sloan et al, *Plasmid* 27, 207 (1992); Genebank M77169). Plasmid pJIR418 was digested with restriction enzyme NdeI. Ligation of the large fragment produced plasmid 1192-23.1. This plasmid lacks a *C. perfringens* origin of replication, but unlike the plasmid 1162-45.1 that was constructed in Example 1, it retains the entire multiple cloning site of pJIR418

In the next step the C-terminal half of the plc gene was sub-cloned into the intermediate plasmid 1192-23.1. Genomic DNA from strain 29 was used as a template for long range PCR. The region of the plc gene (alpha-toxin) from the Bam HI site through a portion of the CPE0038 gene was amplified. The upstream plc primer, 5' CTGGGATCCT-GATACAGATAATAATTTCTCAAAGGAT 3' (SEQ ID NO: 18) corresponds to nucleotides 48880-48916 of strain 13 (Genbank NC 003366). The downstream primer within the CPE0038 gene, 5' actctgcagTTGTCATATCAATTAAAT-TAACTATAATCCC 3' (SEQ ID NO: 19) is complementary to nucleotides 51244-51275 of strain 13 and contains flanking nucleotides including a Pst I restriction site (lowercase). A product of 2402 base pairs was obtained and digested with restriction enzymes Bam HI and Pst I. This fragment was ligated with the large fragment of Bam HI and Pst I digested 1192-23.1 to produce plasmid 1192-36.10.

In the final step the N-terminal half of the plc gene was cloned via PCR. The upstream primer, 5' actgagctcCTAGA-CACTTTGCTTCAATATTTGGGAA 3' (SEQ ID NO: 20) corresponds to nucleotides 46513-46540 of strain 13 and includes flanking nucleotides and a Sac I site (lowercase). The downstream primer, 5' actggatccGCATTCTTATCAT-AATCTGGATAAGTAGAACC 3' (SEQ ID NO: 21) is complementary to nucleotides 48824-48855 of strain 13 and includes flanking nucleotides and a Bam HI site. A 2363 base pair product was produced and this was digested with Sac I and Bam HI restriction enzymes. The digested fragment was ligated with the large fragment of Sac I and Bam HI digested 1192-36.10 to produce plasmid 1192-38.3. Subsequent sequencing of the region flanking the plc Bam HI site in 1192-38.3 confirmed the deletion of nine amino acids from tyr 62 through trp 70.

Plasmid 1192-38.3 was used to electroporate C. perfringens strain 29 cells. Strain 29 was previously shown to transform with an efficiency of 3.6×104 transformants/µg of pJIR418 plasmid DNA. Strain 29 cells were grown and electroporated as in Example 2 with the exception that a liquid selection technique was used after the three hour recovery period. Instead of plating, 0.67 ml aliquots of cells were diluted into 12 ml of TSYC+25 µg/ml chloramphenicol and grown overnight at 37° C. in an anaerobic jar. This modification was used because of the lower transformation and plating efficiencies of strain 29 versus 1240. After overnight growth, cells were diluted again in selection media. Cells from the second grow out were then passed five times without selection prior to plating on blood agar plates. None of the colonies from the blood agar plates were non-hemolytic. Two blood plates were then replica plated to TSYC, TSYC+25 µg/ml chloramphenicol and TSYC+50 µg erythromycin plates. All colonies were erythromycin sensitive but only one of 130 colonies was chloramphenicol sensitive. This colony, 1192-45.4B, was renamed CPERF002. PCR analysis of genomic DNA from CPERF002 with alpha-toxin specific primers showed a positive band for alpha-toxin. This band was smaller than the corresponding band from wild-type strain 29 DNA. Primers specific for the chloramphenicol and erythromycin resistance genes failed to amplify CPERF002 DNA but showed strong positive bands from plasmid 1192-38.3. Sequencing of the CPERFOO2 alpha-toxin confirmed the nine amino acid deletion (see FIG. 3).

CPERF002 was assayed for expression of the inactivated alpha toxoid protein. After 6 hours of anaerobic growth, aliquots of 1 ml of cells were collected and centrifuged. Fifteen microliters of the unconcentrated supernatant media were analyzed by polyacrylamide gel electrophoresis and subjected to Western Blot analysis with a rabbit polyclonal antibody directed against recombinant alpha-toxin protein (Vaccine 11: 1253 (1993)). The results showed specific antibody reactivity with a protein of the expected size for the alpha toxoid protein.

CPERF002 is a genetically engineered deletant strain of C. perfringens Type A. This strain secretes an inactivated toxoid form of the C. perfringens alpha-toxin. Because this strain no longer expresses active alpha-toxin yet retains a significant portion of the toxin's antigenicity, it will be useful as a vaccine to protect against disease caused by C. perfringens.

EXAMPLE 4

C. Perfringens Deletant Vaccines

The CPERF001 and CPERF002 deletant vaccine strains described in Examples 2 and 3 were evaluated for their ability to provide protection against challenge with wild-type C. perfringens. The first part of the study was designed to determine if the administration of the live vaccine strains had any adverse effect on the hatchability of embryonated eggs. The assignment of experimental groups and the safety results are described by Tables 2

TABLE 2

SAFETY RESULTS

| Group* | Vaccine (dose)** | Number of Eggs Hatched (%) |
|---|---|---|
| 1 | CPERF001 ($0.8 \times 10^2$)$^x$ | 18 (90%) |
| 2 | CPERF001 ($0.8 \times 10^3$) | 17 (85%) |
| 3 | CPERF001 ($0.8 \times 10^4$) | 11 (55%) |
| 4 | CPERF001 ($0.8 \times 10^5$) | 16 (80%) |
| 5 | CPERF002 ($1.9 \times 10^2$) | 16 (80%) |
| 6 | CPERF002 ($1.9 \times 10^3$) | 17 (85%) |
| 7 | CPERF002 ($1.9 \times 10^4$) | 14 (70%) |
| 8 | CPERF002 ($1.9 \times 10^5$) | 12 (60%) |
| 9 | Strain 1240 ($1.5 \times 10^3$) | 16 (80%) |
| 10 | Strain 29 ($3.7 \times 10^3$) | 13 (65%) |
| 11 | Media Controls | 19 (95%) |
| 12 | Uninoculated Controls | 18 (90%) |

*20 eggs per group
**100 µl dose given in ovo at 18 days of embryonation (IM)
$^x$Titer per dose is measured as colony forming units (cfu")

At a dose of $10^3$ or less (groups 1,2, 5, and 6), hatchability in these groups was not significantly lower than in the group inoculated with media only (group 11) or the group that was not inoculated (group 12). At the lowest dose CPERF001 showed the same hatchability as the media control and better than the uninoculated control group.

Because the higher doses of the deletants may have had an adverse effect on the hatchability of the eggs, only the two lowest dosage groups for each deletant were included in the efficacy portion of the study. These groups, along with the media control birds (group 11), were challenged with (wild-type) C. perfringens strain CP6 that was administered orally at approximately $10^8$ cfu/ml/bird when the birds were 20, 21 and 22 days of age. All birds were necropsied at 25 days of age and lesions within the small intestine were scored using the rating scale for necrotic enteritis summarized below.

| 0 Score | Necrotic Enteritis 1+ | Necrotic Enteritis 2+ | Necrotic Enteritis 3+ | Necrotic Enteritis 4+ |
|---|---|---|---|---|
| No NE gross lesions on small intestine; intestine has normal elasticity (rolls back on itself after being opened). | Thin and flaccid intestinal wall (intestine remains flat when opened and doesn't roll back into normal position); excess or thickened mucus covering mucus membrane or focal or multifocal mild reddening of the mucosa or congestion of the serosal vessels. | Single or few multifocal areas of reddening and swelling of the intestinal wall; single or few multifocal areas of ulceration or necrosis of the intestinal mucosa. | Extensive multifocal areas of necrosis and ulceration of the intestinal mucosa ± significant hemorrhage or layer of fibrin or necrotic debris on the mucosal surface (Turkish towel appearance). | Dead animal with NE gross lesions scored 2+ or above. |

Scoring with minor modifcations is according to Charles Hofacre, D.V.M., M.A.M., Ph.D., University of Georgia, Poultry Diagnostic and Research Center, 953 College Station Road, Athens, GA 30602, Five (5) birds from the unvaccinated control group (not challenged) were necropsied at the end of the study to confirm there was no exposure to *C. perfringens* during the course of the study. The results are presented in Table 3.

TABLE 3

| | TREATMENT GROUPS FOR PROTECTION* | | | RESULTS | |
|---|---|---|---|---|---|
| Group* | Vaccine | In-ovo Vaccine Dose (cfu) | Days of age at Challenge with *C. perfringens* | N | Mean |
| 1 | CPERF001 | $1 \times 10^2$ | 20, 21 and 22 | 9 | 0.67 |
| 2 | CPERF001 | $1 \times 10^3$ | 20, 21 and 22 | 13 | 0.46 |
| 5 | CPERF002 | $1 \times 10^2$ | 20, 21 and 22 | 12 | 1.33 |
| 6 | CPERF002 | $1 \times 10^3$ | 20, 21 and 22 | 12 | 1.08 |
| 11 | Media control | None | 20, 21 and 22 | 15 | 1.80 |
| 12 | None | None | Not challenged | 5 | 0.00 |

*necropsy at 25 days of age

Scores for Groups 1 and 2 were each statistically significant lower compared to Groups 11 (Wilcoxon Exact Rank Sum Test $p \leq 0.0250$). Mean scores for Groups 5 and 6 were lower than Group 11 but not statistically different (Wilcoxon Exact Rank Sum Test $p \geq 0.2177$). An estimate of vaccine efficacy was performed according to the procedure described by David Siev [*Journal of Modern Applied Statistical Methods* Vol. 4, No. 2, 500-508 (2005)]. Vaccine efficacy in reducing disease severity was estimated at 54% for Group 1, 65% for Group 2, 20% for Group 5 and 27% for Group 6 when compared to Group 11.

EXAMPLE 5

Construction of a *C. Perfringens* Swine Deletant

The strategies used in Examples 1 and 2, supra, are used to construct alpha-toxin deletion mutants from a swine strains of *C. perfringens*. Initially, field isolates from diseased swine are electroporated with plasmid pJIR418 to assess their transformability. Isolates yielding $\geq 10^4$ transformants per microgram of plasmid DNA and susceptible to either chloramphenicol or erythromycin are candidates for deletion.

Genomic DNA from the candidate strains is used as a template for long range PCR of the plc (alpha-toxin) gene and flanking sequences. After subcloning of the PCR products, the alpha-toxin gene and flanking regions are sequenced and restriction mapped. New oligonucleotide primers are synthesized with flanking restriction sites and the products of two separate amplifications are cloned into the suicide plasmid 1192-23.1 to create the 27 base pair deletion as in Example 1.

The swine suicide vector is electroporated into the corresponding swine strain of *C. perfringens* and deletion mutants are isolated using the methods described in Example 2, supra. Deletion mutants are confirmed by the absence of beta hemolysis on blood agar plates and by DNA sequencing of the alpha-toxin gene.

This construct is a genetically engineered deletant strain of *C. perfringens* Type A. This strain secretes an inactivated toxoid form of the *C. perfringens* alpha-toxin. Because this strain no longer expresses active alpha-toxin yet retains a significant portion of the toxin's antigenicity, it is useful as a vaccine to protect swine against disease caused by C. perfringens.

Biological Deposit

Cultures of the following biological materials have been deposited with the following international depository:

American Type Culture Collection (ATCC) 10801 University Boulevard, Manassas, Va. 20110-2209, U.S.A., under conditions that satisfy the requirements of the Budapest Treaty on the International Recognition of the Deposit of Microorganisms for the Purposes of Patent Procedure.

| Organism | Accession No. | Date of Deposit |
|---|---|---|
| *Clostridium perfringens* CPERF/AαToxin 365-054 | PTA7364 | Feb. 7, 2006 |
| *Clostridium perfringens* CPERF/AαToxin 365-053 | PTA7365 | Feb. 7, 2006 |

We claim:

1. An attenuated *Clostridium perfringens* organism constructed by integrating a nucleic acid molecule that encodes a substantially nontoxic mutein of *Clostridium perfringens* alpha-toxin into a chromosome of a non-attenuated *Clostridium perfringens* organism;

wherein the substantially nontoxic mutein alpha-toxin comprises the amino acid sequence of SEQ ID NO: 3 minus at least 9 consecutive amino acid residues, with no more than 24 consecutive amino acid residues deleted;

wherein one of the deleted amino acid residues is $His_{68}$; and wherein the attenuated *Clostridium perfringens* organism is substantially nontoxic due to a lack of a functional wild-type plc gene.

2. The attenuated *Clostridium perfringens* organism of claim 1 wherein the nucleic acid molecule is located at a position on the chromosome that is homologous to the location of a nucleic acid molecule encoding a wild-type alpha-toxin present in the non-attenuated *Clostridium perfringens*.

3. The attenuated *Clostridium perfringens* organism of claim 1 that is a type A *Clostridium perfringens*.

4. The attenuated *Clostridium perfringens* organism of claim 1 wherein the non-attenuated *Clostridium perfringens* from which it was constructed was isolated from a host animal that is either a mammal or an avian.

5. The attenuated *Clostridium perfringens* organism of claim 4, wherein said mammal is selected from the group consisting of bovine, ovine, and porcine.

6. The attenuated *Clostridium perfringens* organism of claim 4 wherein said avian is a chicken, a turkey, a goose, a duck, a swan, a dove, a pigeon, a grouse, or a partridge.

7. A vaccine comprising the attenuated *Clostridium perfringens* organism of claim 1.

8. The vaccine of claim 7 further comprising one or more of the following: a pharmacologically acceptable buffer, excipient, or an adjuvant.

9. A method of reducing the severity of a disease in an animal caused by *C. perfringens* comprising administering to the animal an immunologically effective dose of the vaccine of claim 7.

10. The method of claim 9 wherein the vaccine is administered by one or more of the following routes: oral, intramuscular, intravenous, intradermal, subcutaneous, or intranasal.

11. The method of claim 9 wherein the vaccine is top-dressed on the feed of the animal.

12. The method of claim 9 wherein the vaccine is sprayed onto the animals to provide for oral administration.

13. An animal feed that comprises the vaccine of claim 7.

14. The attenuated *Clostridium perfringens* organism of claim 1 that comprises at least one gene encoding a non-*Clostridium perfringens* polypeptide.

15. The attenuated *Clostridium perfringens* organism of claim 14 wherein said non-*Clostridium perfringens* polypeptide is a non-bacterial polypeptide.

16. The attenuated *Clostridium perfringens* organism of claim 15 wherein the non-bacterial polypeptide is an avian or mammalian polypeptide.

17. The attenuated *Clostridium perfringens* organism of claim 16 wherein the non-bacterial polypeptide is an avian polypeptide.

18. The attenuated *Clostridium perfringens* organism of claim 16 wherein the non-bacterial polypeptide is a cytokine.

19. The attenuated *Clostridium perfringens* organism of claim 18 wherein the cytokine is chicken IL-18.

20. A *Clostridium perfringens* organism that is CPERF/ΔαToxin 365-054 having ATCC Deposit No. PTA7364.

21. A *Clostridium perfringens* organism that is CPERF/ΔαToxin 365-053 having ATCC Deposit No. PTA7365.

22. The attenuated *Clostridium perfringens* organism of claim 1 wherein the substantially nontoxic mutein alpha-toxin comprises the amino acid sequence of SEQ ID NO: 3 with no more than 18 consecutive amino acid residues deleted.

23. An isolated attenuated *Clostridium perfringens* organism constructed by integrating a nucleic acid molecule that encodes a substantially nontoxic mutein of *Clostridium perfringens* alpha-toxin into a chromosome of a non-attenuated *Clostridium perfringens* organism;

wherein the substantially nontoxic mutein alpha-toxin comprises the amino acid sequence of SEQ ID NO: 3 in which 9 consecutive amino acid residues have been deleted;

wherein one of the deleted amino acid residues is $His_{68}$; and wherein the attenuated *Clostridium perfringens* organism is substantially nontoxic due to a lack of a functional wild-type plc gene.

24. The attenuated *Clostridium perfringens* organism of claim 23 wherein the deleted 9 consecutive amino acid residues are amino acids 62 to 70 of the amino acid sequence of SEQ ID NO:3.

25. The attenuated *Clostridium perfringens* organism of claim 24 wherein the deleted 9 consecutive amino acids are replaced by a single leucine residue.

26. A vaccine comprising the attenuated *Clostridium perfringens* organism of claim 25.

27. A vaccine comprising the *Clostridium perfringens* organism of claim 20.

28. A vaccine comprising the *Clostridium perfringens* organism of claim 21.

29. An attenuated *Clostridium perfringens* organism constructed by integrating a nucleic acid molecule that encodes a substantially nontoxic mutein of *Clostridium perfringens* alpha-toxin into a chromosome of a non-attenuated *Clostridium perfringens* organism;

wherein the substantially nontoxic mutein alpha-toxin comprises the amino acid sequence of SEQ ID NO: 3 in which $His_{68}$ is deleted together with an additional 4 to 60 flanking amino acid residues; and wherein the attenuated *Clostridium perfringens* organism is substantially nontoxic due to a lack of a functional wild-type plc gene.

* * * * *